United States Patent [19]
Fuchigami et al.

[11] Patent Number: 5,925,690
[45] Date of Patent: Jul. 20, 1999

[54] DENTAL PRIMER COMPOSITION AND KIT

[75] Inventors: Satoru Fuchigami, Tsukuba; Hideki Ohno, Moriya-cho, both of Japan

[73] Assignee: Tokuyama Corproation, Japan

[21] Appl. No.: 08/977,237

[22] Filed: Nov. 24, 1997

Related U.S. Application Data

[63] Continuation of application No. 08/560,979, Nov. 20, 1995, abandoned.

[51] Int. Cl.$^6$ ...................................................... A61K 6/08
[52] U.S. Cl. .......................... 523/118; 524/547; 524/559; 526/277; 526/318.2
[58] Field of Search ............................ 523/118; 526/277, 526/318.2; 524/547, 559

[56]   References Cited

U.S. PATENT DOCUMENTS

| | | | |
|---|---|---|---|
| 4,806,381 | 2/1989 | Engelbrecht et al. . | |
| 4,810,195 | 3/1989 | Asmussen et al. . | |
| 4,952,613 | 8/1990 | Hosoda . | |
| 5,089,051 | 2/1992 | Eppinger et al. . | |
| 5,145,902 | 9/1992 | Ravet et al. | 524/547 |
| 5,204,383 | 4/1993 | Manabe et al. | 523/118 |
| 5,258,067 | 11/1993 | Podszun et al. . | |
| 5,264,513 | 11/1993 | Ikemura et al. | 523/118 |
| 5,338,773 | 8/1994 | Lu et al. | 523/118 |
| 5,401,783 | 3/1995 | Bowen | 523/118 |

FOREIGN PATENT DOCUMENTS

| | | | |
|---|---|---|---|
| 0 155 812 | 9/1985 | European Pat. Off. . | |
| 0 661 034 A1 | 7/1995 | European Pat. Off. . | |
| 3427220 | 1/1986 | Germany | 524/547 |
| 62-33109 | 2/1987 | Japan . | |
| 62-231652 | 10/1987 | Japan . | |
| 63-279851 | 11/1988 | Japan . | |
| 1-279815 | 11/1989 | Japan . | |
| 6-9327 | 1/1994 | Japan . | |
| 6-24928 | 2/1994 | Japan . | |
| 93/12758 | 7/1993 | WIPO . | |

OTHER PUBLICATIONS

Derwent Publications Ltd., London, GB; AN 94–260386 & JP–A–06 192 030 (Tokuyama Soda KK), Jul. 12, 1994 (abstract).

*Primary Examiner*—Andrew E. C. Merriam
*Attorney, Agent, or Firm*—Wenderoth, Lind & Ponack, L.L.P.

[57]   ABSTRACT

A dental composition which comprises (A) a phosphoric acid group-containing monomer, (B) a carboxylic acid groups-containing monomer and (C) water as main components in amounts of 0.5 to 50% by weight, 1 to 50% by weight and 5 to 90% by weight, based on the composition, respectively; and a dental adhesive kit comprising a dental primer composition containing the monomer (A) and water and an adhesive containing a carboxylic acid-containing polyfunctional monomer and a polymerizable initiator.

13 Claims, No Drawings

DENTAL PRIMER COMPOSITION AND KIT

This application is a continuation of now abandoned application, Ser. No. 08/560,979, filed Nov. 20, 1995, now abandoned.

DETAILED DESCRIPTION OF THE INVENTION

This invention relates to a dental composition suitable for use as a pre-treatment agent for the surface of a tooth, which provides strong adhesion between dental filling materials and a tooth in the restoration of a tooth in the field of dentistry.

Dental filling materials called "composite resin" are mainly used for the restoration of a tooth damaged by dental caries and the like. Generally, this composite resin is filled into a cavity in a tooth, and then polymerized and cured. However, since this material itself has no adhesion to a tooth, a dental adhesive is used together with it. This adhesive is required to have adhesive strength enough to overcome internal stress generated at the time when the composite resin is cured, that is, tensile stress produced in the interface between the composite resin and the tooth. Otherwise, it may not only fall off through its long-term use under extreme oral environment but also have an adverse effect on dental pulp due to entry of bacteria from a gap formed in the interface between the composite resin and the tooth.

The hard tissue of a tooth consists of enamel and dentin, and adhesion to both enamel and dentin is required clinically. Heretofore, a method for pre-treating the surface of a tooth prior to the application of an adhesive has been used to improve adhesion. An aqueous solution of an acid, such as phosphoric acid, citric acid or maleic acid, for decalcifying the surface of a tooth has generally been used as a pre-treatment agent. In the case of enamel adhesion mechanism is said to be mechanical macroscopic retention that an adhesive permeates into a surface roughened by decalcification of an aqueous acid solution and cures, whereas in the case dentin adhesion mechanism is said to be microscopic mechanical retention that an adhesive permeates into extremely small spaces in a sponge-like collagen fiber exposed to the surface of tooth after decalcification and cures. Permeation into the collagen fiber is not so easy as permeation into enamel. Therefore, a permeation promotion agent called "primer" is generally used after treatment with the aqueous acid solution, resulting in cumbersome operation. In order to obtain high adhesive strength to dentin through treatment with the aqueous acid solution only, JP-A-62-33109 (the term "JP-A" as used herein means an "unexamined published Japanese patent application") discloses a tooth surface treatment agent containing a sulfonic acid group-containing polymer, JP-A-62-231652 a tooth surface treatment agent containing a metal halide, JP-A-63-279851 a tooth surface treatment agent comprising an amphoteric amino compound, and JP-A-1-279815 a tooth surface treatment agent comprising an organic carboxylic acid and a metal chloride in combination. However, even when these compositions are used, adhesive strength to dentin is not sufficient. JP-A-6-9327 and JP-A-6-24928 disclose primer compositions which eliminate the need for pre-treatment with an aqueous acid solution. When these compositions are used for dentin, they exhibit a certain measure of adhesive strength. However, when they are used for enamel, their adhesive strength is insufficient because they have a small content of an acidic monomer and decalcification is weak. Inoue et al. propose a primer composition which contains 2-acryloxyethyl hydrogen malate and the like (40th General Meeting of JADR, and 24th and 25th Annual Meeting of the Japanese Society for Dental Materials and Devices). However, when this composition is used, long-term treatment is required and operation is not simplified fully.

In view of these, there has been desired the development of a material which can simplify complicated operation including pre-treatment in which both an aqueous acid solution and a primer are applied and can provide high adhesive strength to both enamel and dentin through a single pre-treatment in cavity restoration operation which comprises steps of pre-treatment, application of an adhesive and restoration of dental filling materials.

It is therefore an object of the present invention to provide a dental composition which provides high adhesive strength to both enamel and dentin with a single treatment.

Another object of the present invention is to provide a dental composition which provides high adhesive strength to a tooth as described above, based on the discovery that a primer composition containing a phosphoric acid group-containing monomer improves adhesive strength to a tooth.

A further object of the present invention is to provide a dental adhesion kit which provides high adhesive strength to both enamel and dentin and is composed of a primer composition comprising a phosphoric acid group-containing monomer as a main effect-developing component and a specific adhesive.

Other objects and advantages of the present invention will become more apparent from the following description.

The above objects and advantages of the present invention can be first attained by a dental composition which comprises (A) a phosphoric acid group-containing monomer, (B) a carboxylic acid groups-containing monomer and (C) water as main components in amounts of 0.5 to 50% by weight, 1 to 50% by weight, and 5 to 90% by weight, based on the composition, respectively.

Preferably, the dental composition of the present invention may further contain (D) a water-soluble organic solvent and/or (G) a polyfunctional monomer.

In the present invention, the weight contents of components (A), (B), (C), (D) and (G) are based on the total of all the components constituting the dental composition, including optional components, if any, that is, the composition.

The phosphoric acid group-containing monomer (A) used in the present invention is not particularly limited, provided that it is a monomer which is an phosphoric acid ester having in one molecule at least one $=P(O)-OH$ group or a functional group that readily reacts with water as an essential component in the present invention to produce at least one $=P(O)-OH$ group, and a polymerizable unsaturated group. Further, a thiophosphoric acid group in which one or two oxygen atoms coupled to a phosphorus atom are substituted by a sulfur atom, or a derivative thereof can be also used.

Typical examples of the phosphoric acid group-containing monomer include phosphoric acid monoesters represented by the following general formula (1), diesters represented by the general formulas (2) and (3), and pyrophosphoric acid ester derivatives in which two of these compounds are condensed in the form of $-P-O-P-$ through an oxygen atom.

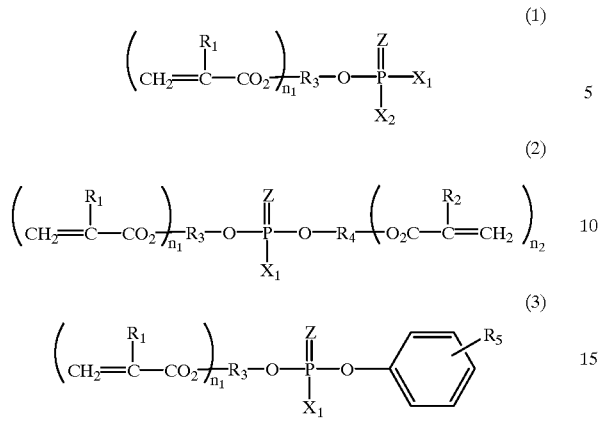

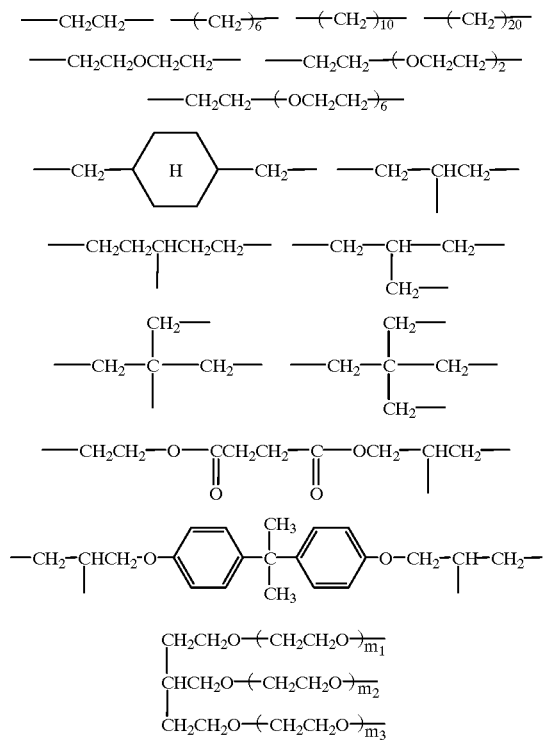

wherein each of $R_1$ and $R_2$ is independently hydrogen atom or a methyl group, each of $R_3$ and $R_4$ is independently an organic group having a valence of 2 to 6 and 1 to 30 carbon atoms, which may have an ether linkage and/or an ester linkage, $R_5$ is hydrogen atom, an alkyl group having 1 to 5 carbon atoms or an alkoxyl group having 1 to 5 carbon atoms, Z is oxygen atom or sulfur atom, each of $X_1$ and $X_2$ is independently selected from the group consisting of hydroxyl group, a mercapto group and a halogen atom, and $n_1$ and $n_2$ are each an integer of 1 to 5.

In the general formulas (1), (2) and (3), $R_3$ and $R_4$ are an organic group having a valence of 2 to 6 and 1 to 30 carbon atoms, which may have an ether linkage and/or an ester linkage. Its structure is not particularly limited, but it is represented by the following formulas.

wherein $m_1$, $m_2$ and $m_3$ are each an integer of 1 or 2.

Preferred examples of the phosphoric acid group-containing monomer represented by the general formula (1) are as follows.

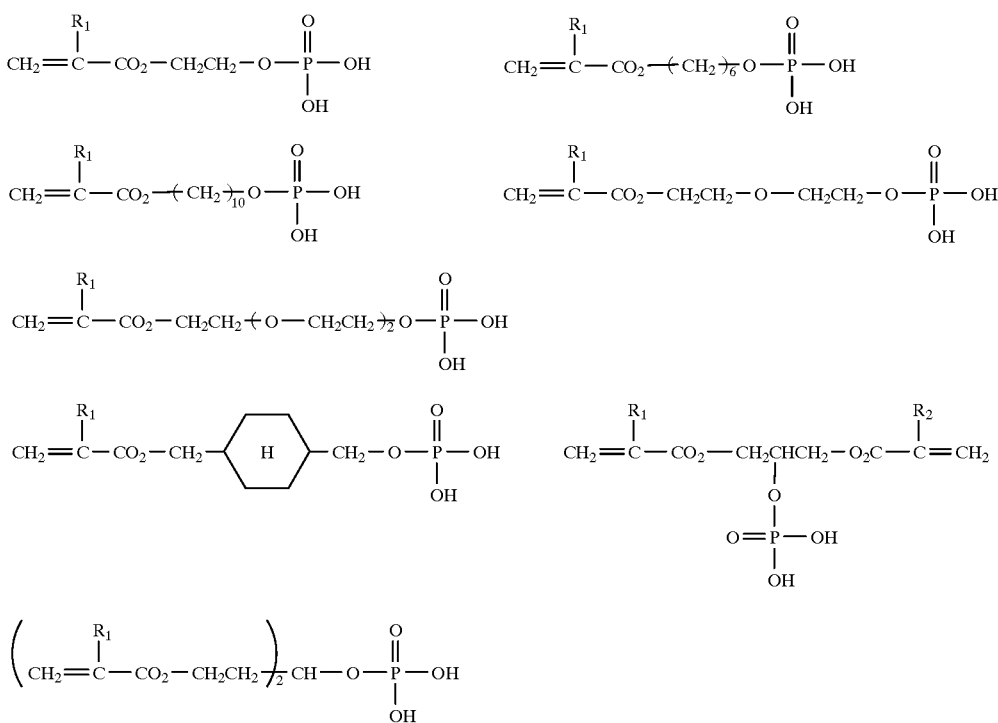

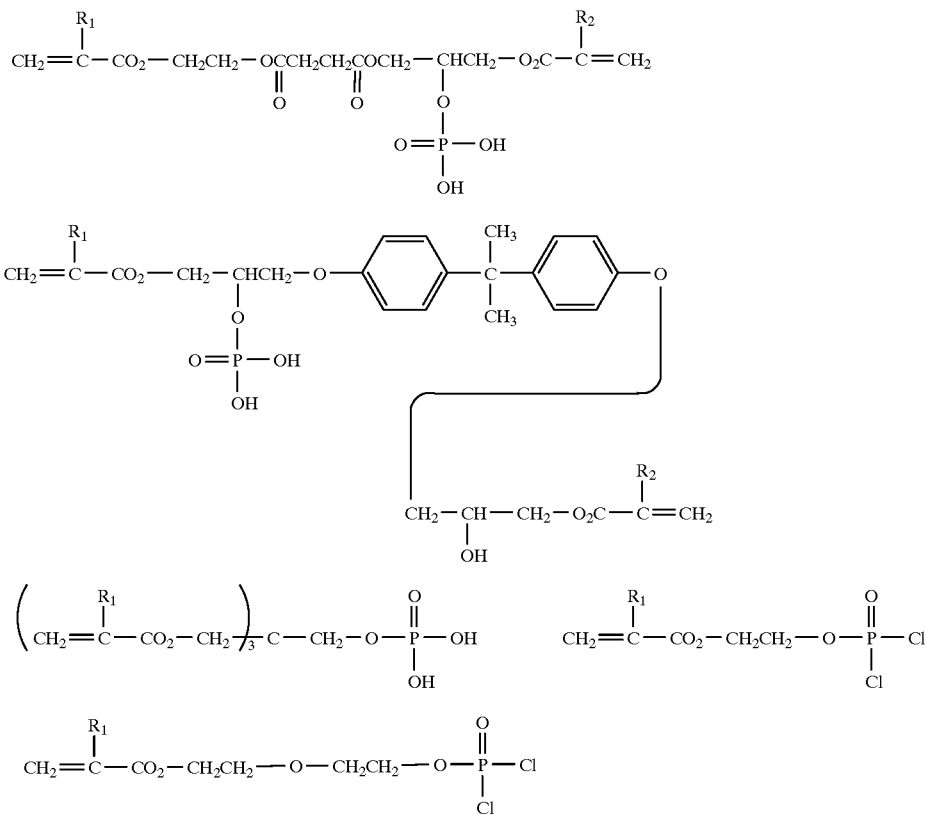
Preferred examples of the phosphoric acid group-containing monomer represented by the general formula (2) are as follows.
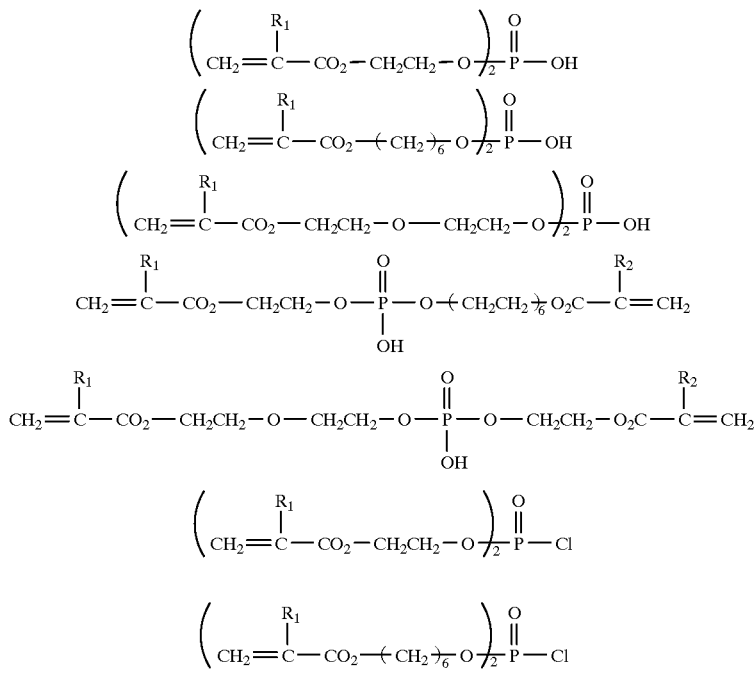

In the general formula (3), $R_5$ is selected from the group consisting of hydrogen atom, an alkyl group having 1 to 5 carbon atoms and an alkoxyl group having 1 to 5 carbon atoms, with examples thereof including methyl, ethyl, propyl, isopropyl, butyl, pentyl, methoxy, ethoxy, propoxy and the like.

Preferred examples of the phosphoric acid group-containing monomer represented by the general formula (3) are as follows.

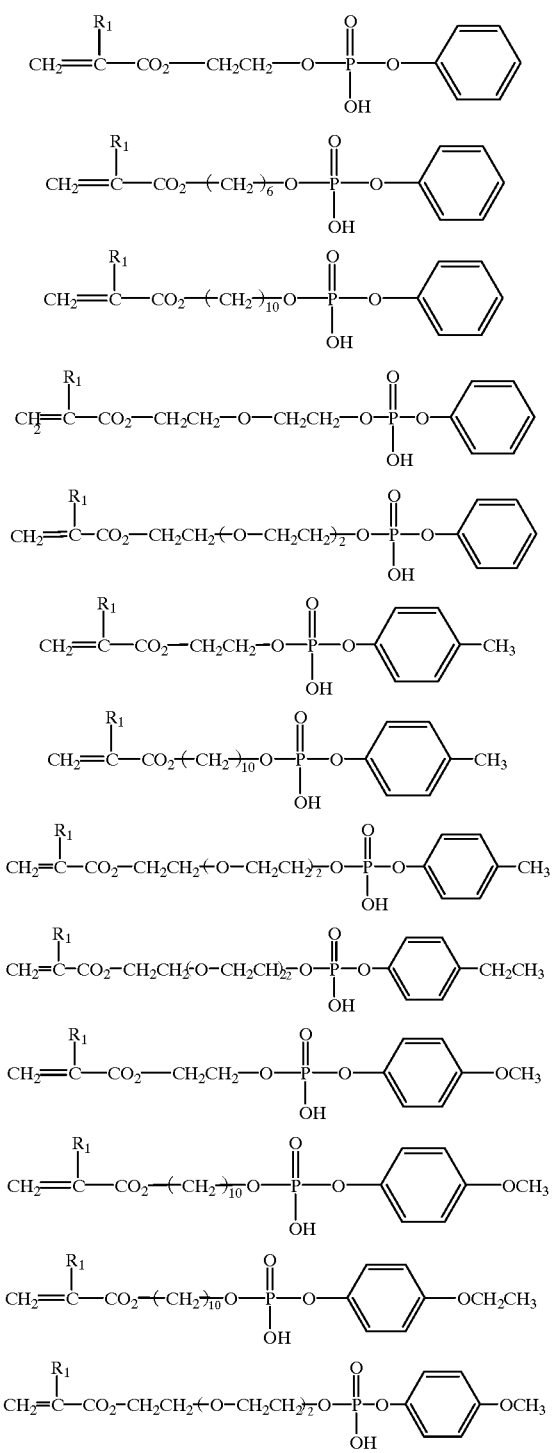

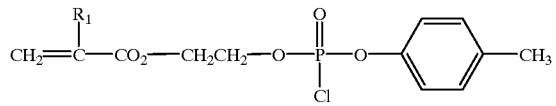
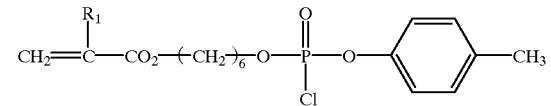
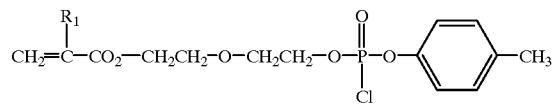

Illustrative examples of the pyrophosphoric acid derivative in which two of the compounds represented by the general formulas (1), (2) and (3) are condensed in the form of —P—O—P— through an oxygen atom are as follows.

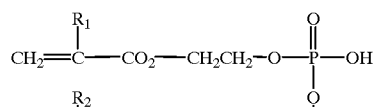
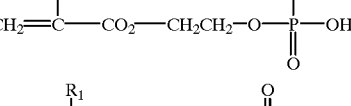
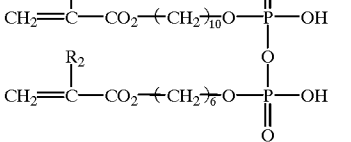
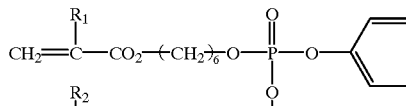
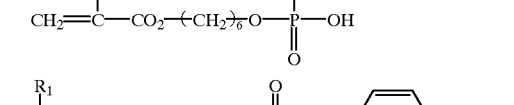
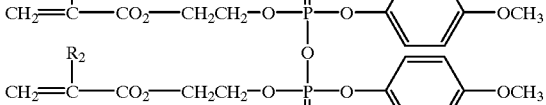
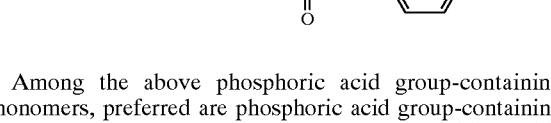

Among the above phosphoric acid group-containing monomers, preferred are phosphoric acid group-containing monomers represented by the general formulas (2) and (3), particularly phosphoric acid group-containing monomers represented by the general formula (3) in which one of the esters is an aromatic ester, from a view point of adhesive strength to a tooth.

A mixture of a plurality of the above phosphoric acid group-containing monomers can be used as required.

The amount of the phosphoric acid group-containing monomer (A) used in the present invention is 0.5 to 50% by weight, preferably 5 to 50% by weight, more preferably 7 to 40% by weight, based on the total of all the constituent components. If the amount of the monomer is too small, adhesive strength to both enamel and dentin, particularly adhesive strength to enamel, will deteriorate, whereas if the amount is too large, adhesive strength to both enamel and dentin, particularly adhesive strength to dentin, will deteriorate.

The carboxylic acid groups-containing monomer (B) of the present invention is a monomer having in one molecule a plurality of carboxyl groups or groups which readily react with water to produce a carboxyl group, such as acid anhydrides or acid halides, and at least one polymerizable unsaturated group.

Illustrative examples of the compound include trimellitic acid derivatives represented by the following general formula (4) and acid anhydrides and acid halides thereof; pyromellitic acid derivatives represented by the following general formula (4) and (5) and acid anhydrides and acid halides thereof; malonic acid derivatives represented by the following general formula (6) and acid anhydrides and acid halides thereof; 6-(meth)acryloxyethylnaphthalene-1,2,6-tricarboxylic acid; N-(meth)acryloylaspartic acid; and the like.

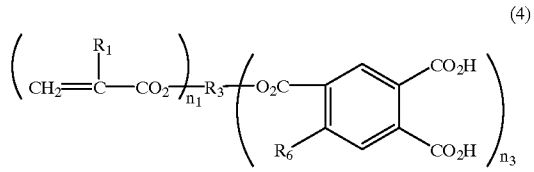
(4)

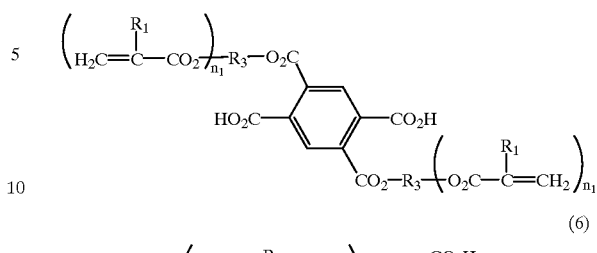
(5)

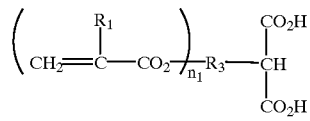
(6)

wherein $R_1$ is hydrogen atom or a methyl group, $R_3$ is an organic group having a valence of 2 to 6 and 1 to 30 carbon atoms, which may have an ether linkage and/or an ester linkage, $R_6$ is hydrogen atom or a carboxyl group, $n_1$ is an integer of 1 to 5, and $n_3$ is 1 or 2.

Preferred examples of the carboxylic acid groups-containing monomer represented by the general formula (4) are as follows.

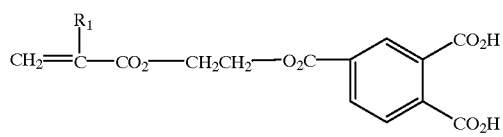
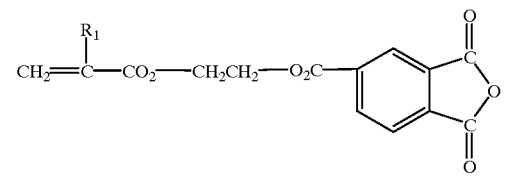

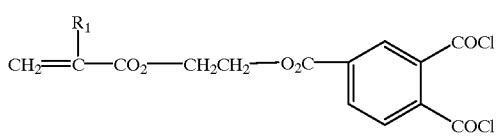
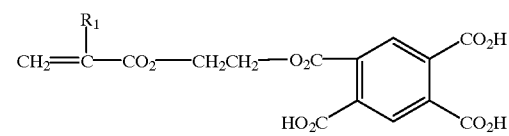

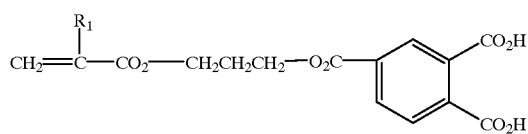
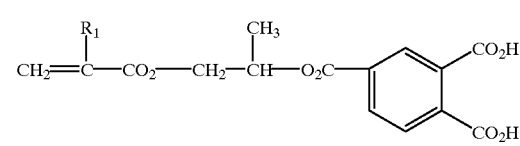

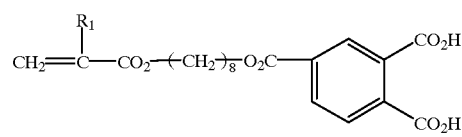
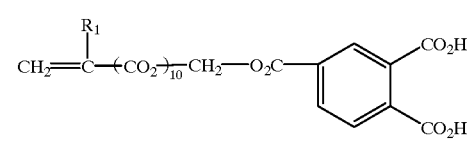

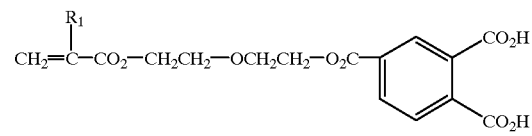
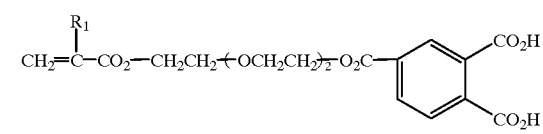

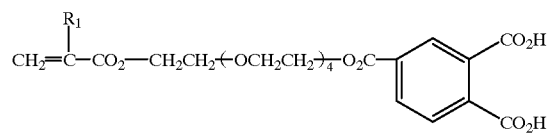
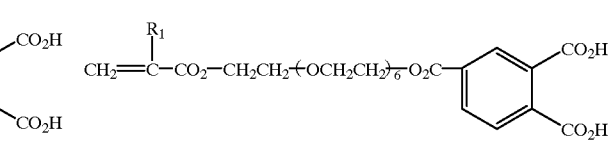

-continued
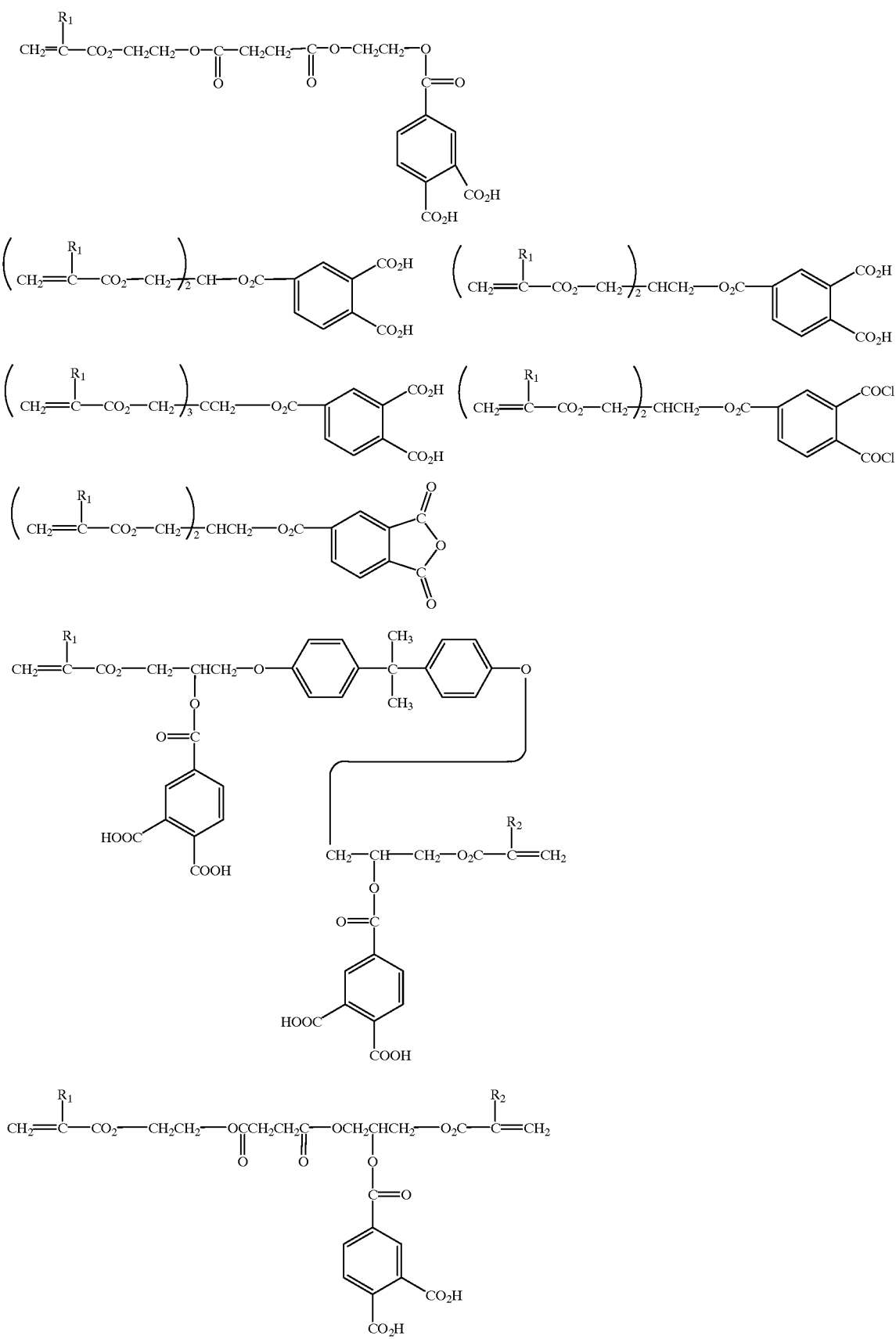

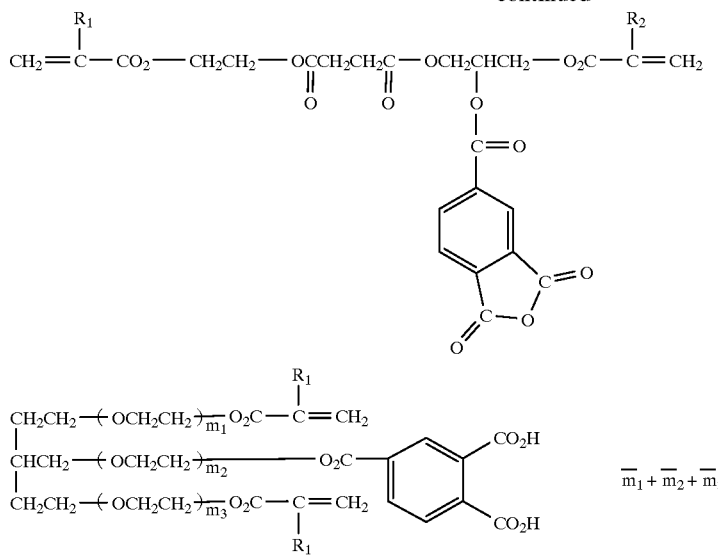
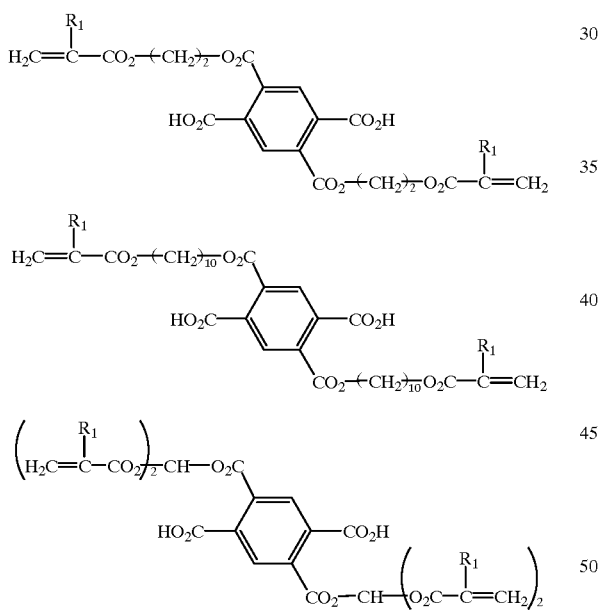
Preferred examples of the carboxylic acid groups-containing monomer represented by the general formula (5) are as follows.
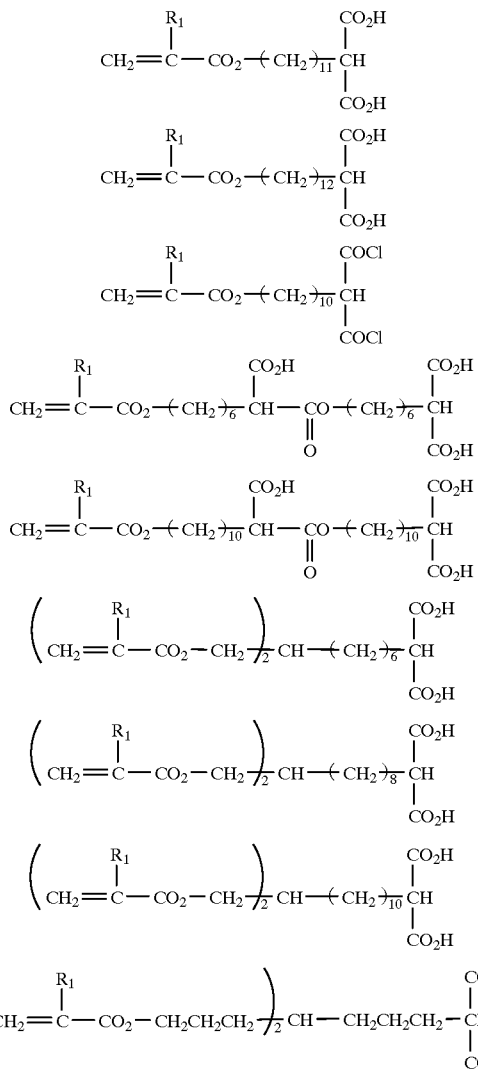
Preferred examples of the carboxylic acid groups-containing monomer represented by the general formula (6) are as follows.
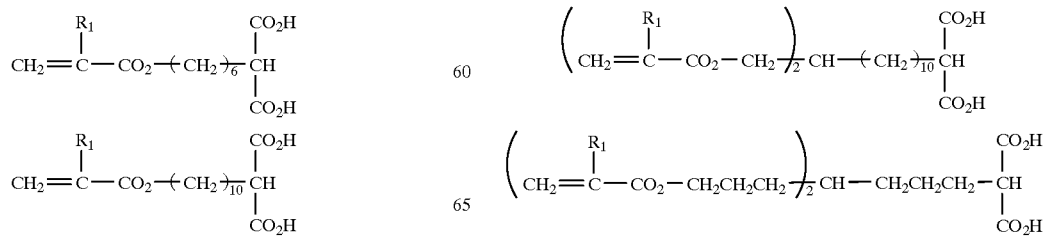

-continued

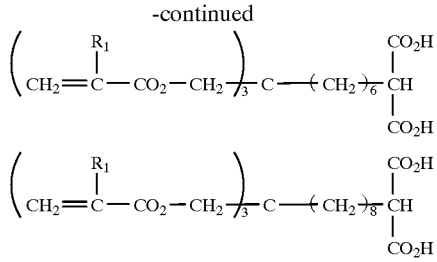

Among the above carboxylic acid groups-containing monomers, preferred from a view point of adhesion to a tooth are monomers which have two carboxyl groups or groups producing a carboxyl group on the same carbon atom or adjacent carbon atoms, and more preferred are trimellitic acid derivatives and malonic acid derivatives.

A mixture of a plurality of the above carboxylic acid groups-containing monomers can be used as required.

The content of the carboxylic acid groups-containing monomer (B) in the present invention is 1 to 50% by weight, preferably 5 to 25% by weight, based on the total of all the constituent components. If the content is below 1% by weight, adhesive strength to dentin will be insufficient, and if the content is above 50% by weight, adhesive strength to both dentin and enamel will deteriorate.

The component (A) and the component (B) are preferably contained in a sum amount of 10% or more by weight, more preferably 15% or more by weight, based on the total of all the constituent components.

Water (C) used in the present invention is necessary for decalcification of a tooth. Preferably, the water contains substantially no impurities which are detrimental to preservation stability, bio adaptability and adhesive property. Examples of the water include deionized water, distilled water and the like. The content of the water (C) in the present invention is 5 to 90% by weight, preferably 20 to 80% by weight, based on the total of all the constituent components. If the content is below 5% by weight, adhesive strength to enamel will be liable to be poor due to insufficient decalcification of a tooth, resulting in insufficient adhesive strength to dentin. If the content is above 90% by weight, adhesive strength to both dentin and enamel will be liable to deteriorate.

The water-soluble organic solvent (D) used in the present invention is preferably blended so as to improve the solubility of the phosphoric acid group-containing monomer, the carboxylic acid groups-containing monomer and monomers as optional components to be described later in a solvent and prepare an uniform solution or an emulsion which is stable for a long time to an extent that there is no problem with its use.

Illustrative examples of the water-soluble organic solvent include alcohol compounds and ether compounds such as methanol, ethanol, 1-propanol, 2-propanol, 1-butanol, 2-butanol, 2-methyl-1-propanol, 2-methyl-2-propanol, 2-methyl-2-butanol, 2-propen-1-ol, 2-propyn-1-ol, 1,2-ethanediol, 1,2-propanediol, 1,3-propanediol, 1,3-butanediol, 1,4-butanediol, 2,3-butanediol, 1,5-pentanediol, hexylene glycol, glycerol, 1,2,6-hexanetriol, trimethylolpropane, diethylene glycol, triethylene glycol, tetraethylene glycol, propylene glycol, dipropylene glycol, tripropylene glycol, 2-methoxyethanol, 2-ethoxyethanol, 2-(methoxyethoxy)ethanol, 2-(ethoxyethoxy)ethanol, triethylene glycol monomethyl ether, triethylene glycol monoethyl ether, 2-isopropoxyethanol, 2-butoxyethanol, 1-methoxy-2-propanol, 1-ethoxy-2-propanol, dipropylene glycol monomethyl ether, tripropylene glycol monomethyl ether, 1,3-dioxolane, tetrahydrofuran, dioxane, propylene oxide, dimethoxymethane, 1,2-dimethoxyethane, 1,2-diethoxyethane, bis(2-methoxyethyl) ether and bis(2-ethoxyethyl) ether; ketone compounds such as acetone and methyl ethyl ketone; phosphoric triamide compounds such as hexamethyl phosphorous triamide; carboxamide compounds such as dimethylformamide and N,N'-dimethylacetamide; carboxylic acid compounds such as acetic acid and propionic acid; oxo-sulfur compounds such as dimethyl sulfoxide and sulforane; and the like. Acrylic acid, methacrylic acid and 2-hydroxyethyl methacrylate having a polymerizable functional group are also acceptable.

Among these water-soluble organic solvents, preferred are alcohol compounds and ether compounds, particularly those which are little detrimental action on living organisms, for example, alcohol compounds and ether compounds such as ethanol, 1-propanol, 2-propanol, 1-butanol, 2-butanol, 2-methyl-1-propanol, 2-methyl-2-propanol, 2-methyl-2-butanol, 2-propene-1-ol, 2-propyn-1-ol, 1,2-ethanediol, 1,2-propanediol, 1,3-propanediol, 1,3-butanediol, 1,4-butanediol, 2,3-butanediol, 1,5-pentanediol, hexylene glycol, glycerol, 1,2,6-hexanetriol, trimethylolpropane, diethylene glycol, triethylene glycol, tetraethylene glycol, propylene glycol, dipropylene glycol, tripropylene glycol, 2-methoxyethanol, 2-ethoxyethanol, 2-(methoxyethoxy)ethanol, 2-(ethoxyethoxy)ethanol, triethylene glycol monomethyl ether, triethylene glycol monoethyl ether, 2-isopropoxyethanol, 2-butoxyethanol, 1-methoxy-2-propanol, 1-ethoxy-2-propanol, dipropylene glycol monomethyl ether, tripropylene glycol monomethyl ether, dimethoxyethane, 1,2-dimethoxyethane, 1,2-diethoxyethane, bis(2-methoxyethyl) ether, bis(2-ethoxyethyl) ether and 2-hydroxyethyl methacrylate; and acetone.

Ethanol and propanol are used the most preferably from a view point of little detrimental action on living organisms. An ether compound having no hydroxyl group is preferably used from a view point of preservation stability of a dental composition.

A mixture of a plurality of the above water-soluble organic solvents can be used as required.

The content of the water-soluble organic solvent (D) of the present invention is preferably 1 to 80% by weight, more preferably 5 to 70% by weight, the most preferably 10 to 40% by weight, based on the total of all the constituent components. If the content is below 1% by weight, the effect of promoting the dispersion and dissolution of the carboxylic acid groups-containing monomer in water will be liable to be insufficient, and if the content is above 80% by weight, adhesive strength to both enamel and dentin will be liable to deteriorate.

Preferably, the dental composition of the present invention further comprises (G) a polyfunctional monomer (G) as described above. Marginal adaptability is enhanced by blending the polyfunctional monomer when the dental composition of the present invention is used as a primer.

The polyfunctional monomer (G) used in the present invention is not particularly limited, provided that it is a monomer having a plurality of polymerizable unsaturated groups in one molecule. A known compound can be used as component (G).

Illustrative examples of the compound include aromatic bifunctional monomers such as 2,2-bis(4-methacryloyloxyphenyl)propane, 2,2-bis(4-(3-methacryloyloxy-2-hydroxypropoxy)phenyl)propane, 2,2-bis(4-methacryloyloxyethoxyphenyl)propane, 2,2-bis(4- methacryloyloxyethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2(4-methacryloyloxyethoxyphenyl)-2(4-methacryloyloxydiethoxyphenyl)propane, 2(4-methacryloyloxydiethoxyphenyl)-2(4-methacryloyloxytriethoxyphenyl)propane, 2(4-methacryloyloxydipropoxyphenyl)-2(4-methacryloyloxytriethoxyphenyl)propane, 2,2-bis(4-methacryloyloxydipropoxyphenyl)propane, 2,2-bis(4-methacryloyloxyisopropoxyphenyl)propane, and acrylates thereof; aliphatic bifunctional monomers such as ethylene glycol dimethacrylate, diethylene glycol dimethacrylate, triethylene glycol dimethacrylate, butylene glycol dimethacrylate, neopentyl glycol dimethacrylate, propylene glycol dimethacrylate, 1,3-butane diol dimethacrylate, 1,4-butane diol dimethacrylate, 1,6-hexane diol dimethacrylate, glycerine dimethacrylate, di-2-methacryloyloxyethyl-2,2,4-trimethyl hexamethylene dicarbamate 1-methacryloyloxymethyl-2-methacryloyloxyethyl hydrogen malate and acrylates thereof; trifunctional monomers such as trimethylolpropane trimethacrylate, trimethylolethane trimethacrylate and trimethylolpropane trimethacrylate and acrylates thereof; tetrafunctional monomers such as pentaerythritol tetramethacrylate and pentaerythritol tetracrylate; and the like.

Among the above polyfunctional monomers, preferred are aliphatic bifunctional monomers, and trifunctional and tetrafunctional monomers.

A mixture of a plurality of the above polyfunctional monomers can be used as required.

The amount of the polyfunctional monomer (G) used in the present invention is preferably 0.1 to 30% by weight, more preferably 0.5 to 20% by weight, based on the total of all the constituent components. If the amount is below 0.1% by weight, no effect of improving marginal adaptability will be liable to be observed, and if the amount is above 30% by weight, adhesive strength to dentin will be liable to deteriorate.

Particularly preferably, the dental composition of the present invention comprises (A) the phosphoric acid group-containing monomer, (B) the carboxylic acid groups-containing monomer, (C) water, (D) the water-soluble organic solvent and (G) the polyfunctional monomer in amounts of 5 to 50% by weight, 1 to 50% by weight, 5 to 90% by weight, 1 to 80% by weight and 0.1 to 30% by weight based on the composition, respectively.

In the composition of the present invention, when the amount of the phosphoric acid group-containing monomer (A) is small, adhesive strength to enamel may not be always sufficient. Adhesive strength to enamel can be improved by blending (E) an inorganic strong acid and/or a non-polymeric organic sulfonic acid or (F) a sulfonic acid group-containing monomer.

As a consequence, according to the present invention, there are provided a dental composition (to be referred to as "second dental composition of the present invention" hereinafter) which comprises (A) a phosphoric acid group-containing monomer, (B) a carboxylic acid groups-containing monomer, (C) water, (D) a water-soluble organic solvent, and (E) an inorganic strong acid and/or a non-polymeric organic sulfonic acid as main components in amounts of 0.5 to 7% by weight, 3 to 50% by weight, 5 to 90% by weight, 1 to 80% by weight and 0.01 to 3% by weight, based on the composition, respectively, and a dental composition (to be referred to as "third dental composition of the present invention" hereinafter) which comprises (A) a phosphoric acid group-containing monomer, (B) a carboxylic acid groups-containing monomer, (C) water, (D) a water-soluble organic solvent and (F) a sulfonic acid group-containing monomer as main components in amounts of 0.5 to 7% by weight, 3 to 50% by weight, 5 to 90% by weight, 1 to 80% by weight and 0.01 to 12% by weight, based on the composition, respectively.

The above descriptions with regards to the above components (A), (B), (C) and (D) can be applied to the second and third dental compositions of the present invention.

In the second dental composition of the present invention, known inorganic strong acids can be used as component (E) with no particular restriction if they have a pKa value in an aqueous solution of 1 or less. In the case of polybasic acids, a value obtained from a dissociation constant of a first stage, that is, $pKa_1$ value, should be 1 or less. Illustrative examples of the acid includes hydrohalogenic acids such as hydrochloric acid and hydrobromic acid; oxo acids such as nitric acid, sulfuric acid, chloric acid, perchloric acid, bromic acid and perbromic acid; and acidic sulfate esters such as methylsulfuric acid and ethylsulfuric acid.

In the second dental composition of the present invention, the non-polymeric organic sulfonic acid (E) is not particularly limited, provided that it is a compound having in one molecule at least one —$SO_3H$ group or at least one functional group which readily reacts with water as an essential component of the present invention to produce a —$SO_3H$ group and known compounds can be used as component (E). Illustrative examples of the compound include position isomers such as methanesulfonic acid, ethanesulfonic acid, propanesulfonic acid, butanesulfonic acid, benzenesulfonic acid, toluenesulfonic acid, xylenesulfonic acid, dodecylbenzenesulfonic acid, chlorobenzenesulfonic acid, bromobenzenesulfonic acid, biphenylsulfonic acid, naphthalenesulfonic acid, anthracenesulfonic acid, phenolsulfonic acid, naphtholsulfonic acid, sulfoacetic acid, sulfobenzoic acid, sulfosalicylic acid, anthraquinone sulfonic acid, benzenedisulfonic acid, naphthalenedisulfonic acid, naphtholdisulfonic acid and biphenyldisulfonic acid; and the like.

Preferably, the above inorganic strong acid and/or the non-polymeric organic sulfonic acid have/has as small a formular weight as possible and as high a volatility as possible from a view point of adhesion to a tooth. Further, those which have a pKa value of 0 or less are more preferred, and nitric acid and hydrochloric acid are the most preferred.

A mixture of a plurality of the inorganic strong acids and/or the non-polymeric organic sulfonic acids can be used as required.

The total amount of the inorganic strong acid and/or the non-polymeric organic sulfonic acid (E) used in the present invention is 0.01 to 3% by weight, preferably 0.5 to 2.5% by weight, based on the total of all the constituent components. If the total amount is below 0.01% by weight, the effect of improving adhesive strength to enamel will be liable to be insufficient, and if the total amount is above 3% by weight, adhesive strength to dentin will be liable to deteriorate.

When the inorganic strong acid and/or the non-polymeric organic sulfonic acid are/is in the form of an aqueous solution like hydrochloric acid and nitric acid, or contain(s) water of crystallization like p-toluenesulfonic acid.1 hydrate, these water contents are calculated as component (C).

Among compounds having a sulfonic acid group, a compound having a polymerizable unsaturated group can be blended in an amount larger than that of the non-polymeric organic sulfonic acid.

In the third dental composition of the present invention, the sulfonic acid group-containing monomer (F) is not particularly limited, provided that it is a monomer having in one molecule at least one —SO$_3$H group or group which readily reacts with water as an essential component of the present invention to produce a —SO$_3$H group and at least one polymerizable unsaturated group. Known compounds can be used as component (F).

Typical examples of the sulfonic acid group-containing monomer include (meth)acrylate derivatives and (meth)acrylamide derivatives of sulfonic acid represented by the following general formula (7), vinylsulfonic acid, styrenesulfonic acid and the like.

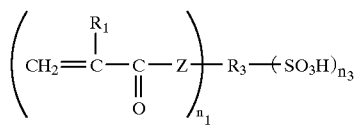
(7)

wherein R$_1$ is hydrogen atom or a methyl group, R$_3$ is an organic group having a valence of 2 to 6 and 1 to 30 carbon atoms, which may have an ether linkage and/or an ester linkage, Z is oxygen atom or an imino group (—NH—), n$_1$ is an integer of 1 to 5, and n$_3$ is 1 or 2.

Preferred examples of the sulfonic acid group-containing monomer represented by the general formula (7) are as follows.

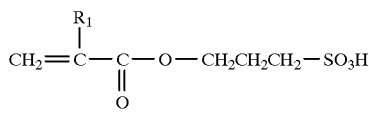

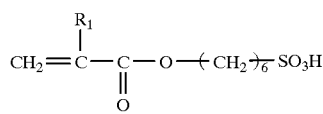

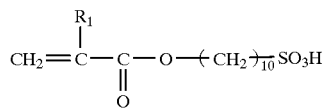

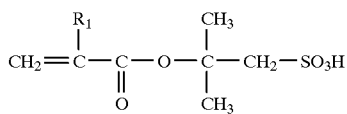

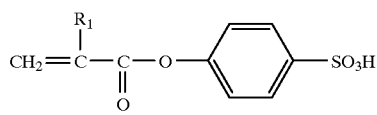

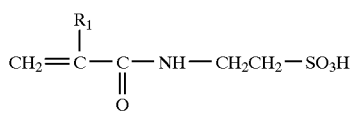

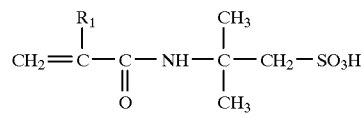

-continued

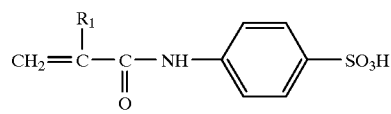

A mixture of a plurality of the above sulfonic acid group-containing monomers can be used as required.

The amount of the sulfonic acid group-containing monomer (F) in the present invention is preferably 0.01 to 12% by weight, more preferably 0.5 to 10% by weight, based on the total of all the constituent components. If the amount is below 0.01% by weight, the effect of improving adhesive strength to enamel will be liable to be insufficient, and if the amount is above 12% by weight, adhesive strength to dentin will be liable to deteriorate.

The sulfonic acid group-containing monomer may be mixed with the inorganic strong acid and/or the non-polymeric organic sulfonic acid illustrated as component (E). In this case, the total amount of the inorganic strong acid and/or the non-polymeric organic sulfonic acid is preferably 3% or less by weight, and the total amount of the inorganic strong acid and/or the non-polymeric organic sulfonic acid and the sulfonic acid group-containing monomer is preferably 12% or less by weight.

The inorganic strong acid and/or the non-polymeric organic sulfonic acid (E) of the second dental composition or the sulfonic acid group-containing monomer (F) of the third dental composition in the present invention need to be added in a state where at least one hydrogen cation can be supplied. When they are neutralized by a metal or amine and added as a neutral salt, they are not component (E) or component (F). Similarly, when a basic substance such as a hydroxide of a metal or an amine is added as an optional component and all or part of the acid is neutralized, the neutralized acid is not component (E) or component (F).

In addition to the above components (A), (B), (C), (D), (E), (F) and (G), the dental composition of the present invention may contain a variety of optional components to be described later as far as they do not impair the effect of the present invention. In this case, the weight contents of the above components (A), (B), (C), (D), (E), (F) and (G) are based on 100% by weight of the total of these components (A), (B), (C), (D), (E), (F), (G) and other optional components.

As described above, the composition of the present invention may contain a monofunctional monomer, a water-insoluble organic solvent, a polymerization initiator, a metal salt, inorganic or organic fine particles and the like within limits not prejudicial to its performance.

Illustrative examples of the monofunctional monomer include monofunctional monomers having no acid group, such as methyl methacrylate, ethyl methacrylate, tetrahydrofurfuryl methacrylate, 2-ethylhexyl methacrylate, 2-hydroxylethyl methacrylate, glycidyl methacrylate, N-methylol methacrylamide, diacetone methacrylamide and acrylates thereof; monocarboxylic acid group-containing monofunctional monomers such as acrylic acid, methacrylic acid, 2-(meth)acryloyloxyethyl hydrogen malate, 2-(meth)acryloyloxyethyl hydrogen succinate and N-(meth)acryloyl-5-aminosalicylic acid; and the like.

Illustrative examples of the water-insoluble organic solvent include hexane, heptane, octane, toluene, dichloromethane, chloroform, carbon tetrachloride, dichloroethane, trichloroethane, pentanone, hexanone, ethyl formate, propyl formate, butyl formate, ethyl acetate, propyl acetate, butyl acetate, vinyl acetate, diethyl ether and the like.

The polymerization initiator may be either a heat polymerization initiator or a photopolymerization initiator.

Preferred examples of the heat polymerization initiator include organic peroxides such as t-butylhydroperoxide, cumenehydroperoxide, di-t-butyl peroxide, dicumyl peroxide, acetyl peroxide, lauroyl peroxide and benzoyl peroxide; azo compounds such as 2,2'-azobis-2-methylbutyronitrile, dimethyl 2,2'-azobisisobutyrate and azobiscyanovaleric acid.

Polymerization can be promoted by using a combination of the above organic peroxide and an amine compound. Preferred examples of the amine compound used as a polymerization promoter include secondary and tertiary amines having an amino group coupled to an aryl group, such as N,N-dimethyl-p-toluidine, N,N-dimethyl aniline, N(2-hydroxyethyl)aniline, N,N-di(2-hydroxyethyl)-p-toluidine, N-methyl aniline, N-methyl-p-toluidine and the like.

It is preferred to further combine a sulfinate or borate with a combination of the organic peroxide and the amine compound. Specific examples of the sulfinate include sodium benzenesulfinate, lithium benzenesulfinate, sodium p-toluenesulfinate, lithium p-toluenesulfinate, potassium p-toluenesulfinate, sodium m-nitrobenzenesulfinate, sodium p-fluorobenzenesulfinate and the like. Specific examples of the borate include sodium salts, lithium salts, potassium salts, magnesium salts, tetrabutyl ammonium salts, tetramethyl ammonium salts and the like of trialkylphenyl boron, trialkyl(p-chlorophenyl)boron, trialkyl(p-fluorophenyl) boron, trialkyl(3,5-bistrifluoromethyl)phenyl boron, dialkyldiphenyl boron, dialkyldi(p-chlorophenyl)boron, dialkyldi(p-fluorophenyl)boron, dialkyldi(3,5-bistrifluoromethyl) phenyl boron, monoalkyltriphenyl boron, monoalkyltri(p-chlorophenyl)boron, monoalkyltri(p-fluorophenyl)boron and monoalkyltri(3,5-bistrifluoromethyl)phenyl boron (alkyl group is n-butyl, n-octyl, n-dodecyl and the like). Polymerization can be started by reacting the sulfinate or the borate with an acid compound.

A photopolymerization initiator (also called "photosensitizer") is preferably used. Illustrative examples of the photopolymerization initiator include α-diketones such as camphorquinone, benzyl, α-naphthyl, acetonaphthene, naphthoquinone, p,p'-dimethoxybenzyl, p,p'-pichlorobenzyl acetyl, 1,2-phenanthrenequinone, 1,4-phenanthrenequinone, 3,4-phenanthrenequinone and 9,10-phenanthrenequinone; thioxanthones such as 2,4-diethyl thioxanthone; α-aminoacetophenones such as 2-benzyl-dimethylamino-1-(4-morpholinophenyl-butanone-1,2-benzyl-diethylamino-1-(4-morpholinophenyl-butanone-1,2-benzyl-dimethylamino-1-(4-morpholinophenyl)-propanone-1,2-benzyl-diethylamino-1-(4-morpholinophenyl)-propanone-1,2-benzyl-dimethylamino-1-(4-morpholinophenyl)-pentanone-1, and 2-benzyl-diethylamino-1-(4-morpholinophenyl)pentanone-1; and the like.

Further, it is preferred to use a combination of the above photosensitizer and a photopolymerization promoter. Illustrative examples of the photopolymerization promoter include tertiary amines such as N,N-dimethyl aniline, N,N-diethyl aniline, N,N-di-n-butyl aniline, N,N-dibenzyl aniline, N,N-dimethyl-p-toluidine, N,N-diethyl-p-toluidine, N,N-dimethyl-m-toluidine, p-bromo-N,N-dimethyl aniline, m-chloro-N,N-dimethyl aniline, p-dimethylaminobenzaldehyde, p-dimethylaminoacetophenone, p-dimethylaminobenzoic acid, p-dimethylaminobenzoic acid ethyl ester, p-dimethylaminobenzoic acid methyl ester, N,N-dimethylanthranilic acid methyl ester, N,N-dihydroxyethyl aniline, N,N-dihydroxyethyl-p-toluidine, p-dimethylaminophenethyl alcohol, p-dimethylamino stilbene, N,N-dimethyl-3,5-xylidine, 4-dimethylaminopyridine, N,N-dimethyl-α-naphthylamine, N,N-dimethyl-β-naphthylamine, tributyl amine, tripropyl amine, triethyl amine, N-methyldiethanol amine, N-ethyldiethanol amine, N,N-dimethylhexyl amine, N,N-dimethyldodecyl amine, N,N-dimethylstearyl amine, N,N-dimethylaminoethyl methacrylate, N,N-diethylaminoethyl methacrylate and 2,2'-(n-butylimino)diethanol; barbituric acids such as 5-butylbarbituric acid and 1-benzyl-5-phenylbarbituric acid; and the like.

Organic boron compounds which react with oxygen or water to produce a radical, such as tributyl borane and tributyl borane partial oxides are organic metal type polymerization initiators.

The above heat polymerization initiator, photosensitizer, sulfinate, borate, polymerization promoter and organic metal type polymerization initiator can be used alone or in combination as required.

Metal salts include hydrochloric acid salts, hydrofluoric acid salts, sulfuric acid salts, nitric acid salts, phosphoric acid salts, acetic acid salts, citric acid salts, oxalic acid salts, EDTA salts and the like of polyvalent metals such as magnesium, aluminum, calcium, iron, cobalt, nickel, copper, zinc, strontium, tin and barium.

The viscosity and flowability of the dental composition can be controlled by blending inorganic or organic fine particles.

Illustrative examples of the inorganic fine particle include polymer fine particles such as polyethylene, polypropylene, polymethyl methacrylate, polyamides, polyesters, polystyrenes and silicones; single or double oxides of metals such as silicon, aluminum, titanium zirconium, nickel, cobalt, strontium, iron, copper, zinc, tin, magnesium, calcium, potassium and sodium; nitrides such as silicon nitride, aluminum nitride, titanium nitride and boron nitride; carbides such as silicon carbide and boron carbide; and the like. Fine particles prepared by surface-treating these inorganic fine particles with silane coupling agents such as methyltrimethoxysilane, methyltriethoxysilane, methyltrichlorosilane, dimethyldichlorosilane, trimethylchlorosilane, vinyltrimethoxysilane, vinyltriethoxysilane, vinyltrichlorosilane, vinyltriacetoxysilane, vinyltris(β-methoxyethoxy)silane, γ-methacryloxypropyltrimethoxysilane, γ-methacryloxypropyltris(β-methoxyethoxy)silane, γ-chloropropyltrimethoxysilane, γ-chloropropylmethyldimethoxysilane, γ-glycidoxypropyltrimethoxysilane, γ-glycidoxypropylmethyldiethoxysilane, β(3,4-epoxycyclohexyl)ethyltrimethoxysilane, N-phenyl-γ-aminopropyltrimethoxysilane and hexamethyldisilazane; titanate coupling agents such as isopropyltriisostearoyl titanate, isopropyltrioctanoyl titanate, isopropylisostearoyldiacryl titanate, isopropyltridodecylbenzenesulfonyl titanate, isopropyldimethacrylisostearoyl titanate and isopropyltricumylphenyl titanate; aluminum-based coupling agents such as acetoalkoxy aluminum diisopropylate may also be used. Further, fine particles prepared by coating the surfaces of the inorganic fine particles with polymers such as polyethylene, polypropylene, polymethyl methacrylate, polyamides, polyesters, polystyrenes, silicones and the like may be also preferably used.

The method for producing the inorganic fine particle is not particularly limited, and conventional co-precipitation, spray coating, sol-gel and bulk pulverization-classification methods can be used. The surface treatment method is not particularly limited, and conventional spray drying, dry mixing and wet mixing methods can be used without any restriction.

The primary particle diameter of the fine particle is preferably 0.001 to 1 μm. It is actually difficult to obtain particles having a diameter of 0.001 μm or less. On the other hand, when the particle diameter is too large, there is a problem that precipitation readily occurs, making uniform dispersion difficult. Therefore, the particle diameter is preferably 0.5 μm or less, more preferably 0.1 μm or less.

A mixture of a plurality of the fine particles which are different in composition, shape, production method, surface treatment method and particle diameter may be used.

A coloring matter may be blended with the fine particle as a coloring material.

The method for preparing the dental composition of the present invention is not particularly limited. The above phosphoric acid group-containing monomer, carboxylic acid groups-containing monomer, water, water-soluble organic solvent, inorganic strong acid and/or non-polymeric organic sulfonic acid or sulfonic acid group-containing monomer and as required, optional components are charged into a container in desired proportions, stirred and mixed together to obtain an uniform solution or an emulsion.

The package of the composition of the present invention can be suitably determined under the condition that it does not impair preservation stability. For instance, a solution comprising a phosphoric acid group-containing monomer, carboxylic acid groups-containing monomer and water-soluble organic solvent as main components and a solution comprising an inorganic strong acid and/or a non-polymeric organic sulfonic acid, or a sulfonic acid group-containing monomer, and water as main components can be packaged separately and mixed at the time of use.

As described above, the most characteristic feature of the dental composition of the present invention is that it comprises the phosphoric acid group-containing monomer and it needs to comprise the above monomer, the carboxylic acid groups-containing monomer and water.

Studies conducted by the inventors of the present invention have revealed that, even if a dental composition has the above composition excluding the carboxylic acid groups-containing monomer, it exhibits excellent adhesion to a tooth when it is used in conjunction with a specific adhesive.

Therefore, according to the present invention, there are further provided a dental adhesive kit (to be referred to as "first kit of the present invention" hereinafter) which comprises a dental primer composition comprising (A) a phosphoric acid group-containing monomer in an amount of 5 to 50% by weight, based on the composition, and (C) water as main components and an adhesive comprising (H) a carboxylic acid groups-containing polyfunctional monomer and (I) a polymerization initiator; and a dental adhesive kit (to be referred to as "second kit of the present invention" hereinafter) which comprises a dental primer composition comprising of (A) a phosphoric acid group-containing monomer in an amount of 5 to 50% by weight, based on the primer composition, and (C) water as main components and an adhesive comprising (J) a carboxylic acid groups-containing monofunctional monomer, (K) a water-soluble hydroxyl group-containing monomer, (G) a polyfunctional monomer and (I) a polymerization initiator.

The phosphoric acid group-containing monomer (A) used in the dental primer composition which comprises the phosphoric acid group-containing monomer and water (C) as main components is identical to component (A) illustrated for the afore-mentioned dental composition.

Among the afore-mentioned examples of the phosphoric acid group-containing monomer, preferred are phosphoric acid group-containing monomers represented by the general formulas (2) and (3), particularly phosphoric acid group-containing monomers represented by the general formula (3) in which one of the esters is an aromatic ester.

A mixture of a plurality of the above phosphoric acid group-containing monomers can be used as required.

The amount of the phosphoric acid group-containing monomer (A) used in the dental primer composition which does not contain component (B) is 5 to 50% by weight, preferably 7 to 40% by weight, based on the primer composition. If the amount is too small, adhesive strength to both dentin and enamel will deteriorate, and if the amount is too large, adhesive strength to both dentin and enamel, particularly adhesive strength to dentin, will deteriorate.

The water (C) used in the dental primer composition is identical to component (C) illustrated for the afore-mentioned dental composition.

Preferably, the dental primer composition further comprises (D) a water-soluble organic solvent, (E) an inorganic strong acid and/or a non-polymeric organic sulfonic acid, (F) a sulfonic acid group-containing monomer, and (G) a polyfunctional monomer as required.

Preferred examples and amounts of components (D), (E), (F) and (G) are the same as those described for the afore-mentioned dental composition.

Monofunctional monomer, water-insoluble organic solvent, polymerization initiator, metal salt and inorganic or organic fine particle above-illustrated as optional components may be added.

The method for preparing the above dental primer composition and the package of the dental primer composition are not particularly limited, and are the same as those described for the afore-mentioned dental composition.

The adhesive used in conjunction with the dental primer composition comprises (H) a carboxylic acid groups-containing polyfunctional monomer and (I) a polymerization initiator in the first kit.

The carboxylic acid groups-containing polyfunctional monomer (H) is a monomer which has in one molecule a plurality of carboxylic acids or groups which readily react with water to produce a carboxyl group, such as anhydrides and acid halides thereof, and a plurality of polymerizable unsaturated groups.

Illustrative examples of such a compound include compounds having a plurality of polymerizable unsaturated groups, out of the compounds specified as examples of the afore-mentioned carboxylic acid groups-containing monomer. Among these carboxylic acid groups-containing polyfunctional monomers, preferred are monomers having two carboxyl groups or two groups producing a carboxyl group on the same carbon atom or adjacent carbon atoms, and more preferred are trimellitic acid derivatives represented by the above general formula (4) in which n3 is an integer of 2 to 4.

A mixture of a plurality of these carboxylic acid groups-containing polyfunctional monomers can be used as required.

The adhesive can further contain other monomers to be described later as optional components. In this case, the weight content of the above carboxylic acid groups-containing polyfunctional monomer is based on 100 parts by weight of the total of the carboxylic acid groups-containing polyfunctional monomer and other monomers contained as optional components (to be referred to as "100 parts by weight of the total of all monomers" hereinafter).

When other monomers are contained as optional components, the amount of the carboxylic acid groups-containing polyfunctional monomer (H) is preferably 5 to 95 parts by weight, more preferably 10 to 90 parts by weight, from a view point of adhesion to a tooth.

Since the above carboxylic acid groups-containing polyfunctional monomer contained in the adhesive is generally a liquid having high viscosity or solid other monomers to be described later are preferably mixed with the monomer as optional components from a view point of operability. Further, since the above carboxylic acid groups-containing polyfunctional monomer is generally expensive, other inexpensive monomers are preferably added as optional components to dilute the above monomer.

Illustrative examples of the other monomers include carboxylic acid groups-containing monofunctional monomers, water-soluble hydroxyl group-containing monomers and polyfunctional monomers which are described hereinafter, phosphoric acid group-containing monomers specified in the section for the afore-mentioned dental composition, monofunctional monomers having no acid group specified as optional components, monocarboxylic acid group-containing monofunctional monomers and the like. A mixture of a plurality of these monomers can be used as required.

The other adhesive used in conjunction with the afore-mentioned dental primer composition comprises (J) a carboxylic acid groups-containing monofunctional monomer, (K) a water-soluble hydroxyl group-containing monomer, (G) a polyfunctional monomer, and (I) a polymerization initiator in the second kit.

The carboxylic acid groups-containing monofunctional monomer (J) is a monomer having in one molecule a plurality of carboxyl groups or groups which readily react with water to produce a carboxylic acid, such as acid anhydrides or acid halides thereof, and one polymerizable unsaturated group.

Illustrative examples of such a compound include compounds having one polymerizable unsaturated group, out of the compounds specified as examples of the afore-mentioned carboxylic acid groups-containing monomer (B). Among these carboxylic acid groups-containing monofunctional monomers, preferred are malonic acid derivatives represented by the general formula (5) in which $n_1$ is 1.

A mixture of a plurality of these carboxylic acid groups-containing monofunctional monomers can be used as required.

The content of the carboxylic acid grounds-containing monofunctional monomer contained in the adhesive is preferably 5 to 60 parts by weight, more preferably 10 to 50 parts by weight, based on the 100 parts by weight of the adhesive, from a view point of adhesion to a tooth.

The water-soluble hydroxyl group-containing monomer (K) is a water-soluble monomer having at least one hydroxyl group and at least one polymerizable unsaturated group in one molecule. Known compounds can be used without restrictions if they have such a structure. In this case, when 10 g of a hydroxyl group-containing monomer and 100 g of water are mixed at a temperature of 25° C. and are thoroughly uniformly mixed with each other, the hydroxyl group-containing monomer is considered as water-soluble.

Illustrative examples of such a compound include (meth) acrylic acid esters of polyhydric alcohols and polyethylene glycols such as 2-hydroxyethyl methacrylate, 2-hydroxypropyl methacrylate, 3-hydroxypropyl methacrylate, 2,3-dihydroxypropyl methacrylate, 2,3-dihydroxybutyl methacrylate, 2,4-dihydroxybutyl methacrylate, 2-hydroxymethyl-3-hydroxypropyl methacrylate, 2,3,4-trihydroxybutyl methacrylate, 2,2-bis (hydroxymethyl)-3-hydroxypropyl methacrylate, 2,3,4,5-tetrahydroxypentyl methacrylate, diethylene glycol monomethacrylate, triethylene glycol monomethacrylate, tetraethylene glycol monomethacrylate, pentaethylene glycol monomethacrylate and acrylates thereof; (meth)acryl amides of amino alcohols such as N-methylolmethacryl amide and N-methylolacryl amide; and the like.

Among the above water-soluble hydroxyl group-containing monomers, preferred are 2-hydroxyethyl methacrylate and 2,3-dihydroxypropyl methacrylate from a view point of adhesion to a tooth and a cost.

A mixture of a plurality of these water-soluble hydroxyl group-containing monomers can be used as required.

The content of the above water-soluble hydroxyl group-containing monomer contained in the adhesive of the present invention is preferably 5 to 50 parts by weight, more preferably 10 to 40 parts by weight, based on 100 parts by weight of the total of all monomers, from a view point of adhesion to a tooth.

The polyfunctional monomer (G) is not particularly limited, provided that it is a monomer having a plurality of polymerizable unsaturated groups in one molecule. Known compounds can be used as component (G).

Illustrative examples of such a compound include the polyfunctional monomer (G) illustrated in the section of the afore-mentioned dental composition. The afore-mentioned carboxylic acid groups-containing polyfunctional monomers and monomers having a plurality of polymerizable unsaturated groups among the afore-mentioned phosphoric acid group-containing monomers (A) may also be preferably used.

A mixture of a plurality of these polyfunctional monomers can be used as required.

The content of the above polyfunctional monomer (G) contained in the adhesive of the present invention is preferably 20 to 90 parts by weight, more preferably 30 to 80 parts by weight, based on 100 parts by weight of the total of all monomers, from a view point of adhesion to a tooth.

In addition to the above carboxylic acid groups-containing monofunctional monomer, water-soluble hydroxyl group-containing monomer and polyfunctional monomer, the adhesive of the present invention may contain other monomers for the purpose of saving costs and improving operability by adjusting the viscosity of the adhesive.

The other monomers include the phosphoric acid group-containing monomers specified in the section of the afore-mentioned dental composition, the monofunctional monomers having no acid group and monocarboxylic acid group-containing monofunctional monomers specified as optional components. A mixture of a plurality of these monomers can be used as required.

The above two adhesives of the present invention contain (I) a polymerization initiator for polymerization and curing. The polymerization initiator is not particularly limited and known polymerization initiators can be used without restriction.

Illustrative examples of the polymerization initiator include heat polymerization initiators such as organic peroxides and azo compounds specified as optional components for the afore-mentioned dental composition, photosensitizers such as α-diketones, thioxanthones and α-aminoacetophenones, and organic metal type polymerization initiators. A mixture of a plurality of these polymerization initiators can be used as required.

The amount of the polymerization initiator added is not particularly limited, provided it exhibits its effect. The amount is preferably 0.01 to 20 parts by weight, more preferably 0.05 to 10 parts by weight, based on 100 parts by weight of the total of all monomers.

The heat polymerization initiator and the photosensitizer are preferably used in combination with an appropriate polymerization promoter.

Illustrative examples of the polymerization promoter include secondary and tertiary amines, sulfinates, borates, barbituric acids and the like specified as optional components for the afore-mentioned dental composition. A mixture of a plurality of these polymerization promoters can be used as required.

The amount of the polymerization promoter is not particularly limited, provided it exhibits its effect. The amount is preferably 0.01 to 20 parts by weight, more preferably 0.05 to 10 parts by weight, based on 100 parts by weight of the total of all monomers.

The above adhesives of the present invention preferably contain a slight amount of a polymerization inhibitor such as hydroquinone, hydroquinone monomethyl ether and butylhydroxy toluene.

Preferably, a filler is further added to the adhesives of the present invention as required. It is possible to improve the mechanical strength and control the viscosity and flowability of the adhesives by adding the filler.

Illustrative examples of the filler include polymer fine particles, inorganic fine particles such as metal oxides, metal nitrides and metal carbides, and fine particles prepared by treating the surfaces thereof with silane coupling agents, titanate coupling agents and aluminate coupling agents, as specified as an optional component for the afore-mentioned dental composition.

Further, since the viscosity of the adhesive is relatively high, the possibility of filler sedimentation is reduced. Therefore, particles having a particle diameter larger than those of the above fine particles can be used. For instance, polymer or inorganic compounds having a particle diameter of 1 to 200 $\mu$m can be used.

A filler prepared by dispersing organic or inorganic particles in a monomer, polymerizing them and pulverizing a particle dispersion polymer to achieve a particle diameter of 200 $\mu$m or less can be used.

The particle diameter of the filler is preferably 0.001 to 200 $\mu$m, more preferably 0.001 to 100 $\mu$m.

A mixture of a plurality of fillers which are different in composition, shape, production method, surface treatment method and particle diameter can be used.

The amount of the filler is not particularly limited, provided that it does not impair the effect of the present invention, but it is preferably 300 parts or less by weight, more preferably 100 parts or less by weight, based on 100 parts by weight of the total of all monomers.

The method for preparing the adhesive of the present invention is not particularly limited. The above carboxylic acid groups-containing polyfunctional monomer or carboxylic acid groups-containing monofunctional monomer, water-soluble hydroxyl group-containing monomer, polyfunctional monomer, polymerization initiator and optional components to be blended as required are weighed in desired proportions, and mixed together, while stirring to prepare an uniform solution.

The dental composition of the present invention is used as a pre-treatment agent in dental restoration operation which consists of application of the pre-treatment agent to the surface of a tooth, drying, application of an adhesive, curing of the adhesive, restoration of dental filling materials and curing of the dental filling material. Supposing the mechanism that an inorganic component contained in a tooth is dissolved by application of the pre-treatment agent to the surface of the tooth and a permeation layer of the monomers is formed in the tooth at the same time, permeation, dispersion and polymerization of an adhesive to be subsequently applied are facilitated, and a strong adhesive layer is formed, the phosphoric acid group-containing monomer dissolves an inorganic component due to the acid supply capability of its phosphoric acid group and permeates easily into a tooth due to its affinity for a tooth at a phosphoric acid group site. Therefore, it is advantageous for the formation of a permeation layer of the monomer in the tooth. The monomer having a plurality of carboxylic acid groups is assumed to make more advantageous the formation of the permeation layer of the monomer in a tooth due to its high affinity for a tooth. Further, the inorganic strong acid and/or non-polymeric organic sulfonic acid, or the sulfonic acid group-containing monomer are/is considered to ensure the dissolution of the inorganic component due to its acid supply capability.

In bonding a tooth and dental filling materials by means of an adhesive, the composition of the present invention is used as a pre-treatment agent for the surface of a tooth prior to the adhesive, thereby reducing the number of pre-treatment steps to one. As a result, conventional complicated pre-treatment operation for the surface of the tooth which requires two steps consisting of treatment with an aqueous acid solution and application of a primer can be simplified and further high adhesive strength to both enamel and dentin can be obtained.

The composition of the present invention will be further described with the following examples. However, it is understood that the present invention is not intended to be limited to these examples. Abbreviations, a method for measuring adhesive strength and a method for preparing an adhesive shown in the text and examples are as follows.

(1) abbreviations
Component (A)
  PM: 2-methacryloyloxyethyl dihydrogen phosphate
  Phenyl-P: 2-methacryloyloxyethyl phenyl hydrogen phosphate
  PM2: bis(2-methacryloyloxyethyl)hydrogen phosphate
Component (B)
  MTS: 2-methacryloyloxyethyl-3'-methacryloyloxy-2'-(3,4-dicarboxybenzoyloxy)propyl succinate
  MAC-10: 11-methacryloyloxy-1,1-undecanedicarboxylic acid
  4-META: 4-methacryloyloxyethyl trimellitate anhydride
Component (D)
  IPA: isopropyl alcohol
  DME: 1,2-dimethoxy ethane
  BMEE: bismethoxyethyl ether
  HEMA: 2-hydroxyethyl methacrylate
Component (E)
  DBS: dodecylbenzenesulfonic acid
Component (F)
  AMPS: 2-acrylamide-2-methylpropanesulfonic acid
Component (G)
  3G: triethylene glycol dimethacrylate
  NPG: neopentyl glycol dimethacrylate
  Bis-GMA: 2,2-bis(4-(2-hydroxy-3-methacryloyl-oxypropoxy)phenyl)propane D-2.6E: the following compounds

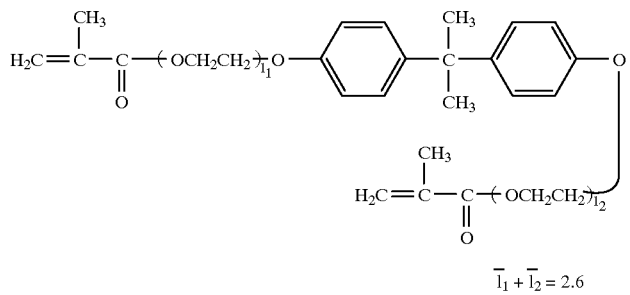

$\bar{l}_1 + \bar{l}_2 = 2.6$

Component (H)
  MTS: 2-methacryloyloxyethyl-3'-methacryloyloxy-2'-(3,4-dicarboxybenzoyloxy)propyl succinate
  4-TAPT: 4-(3-acryloxy-2,2-bis(acryloxymthyl)propyl) dihydrogen trimellitate
Component (I)
  CQ: camphorquinone
  DMBE: ethyl 4-dimethylamino benzoate
  DAAP: 4'-dimethyl aminoacetophenone
Component (J)
  MAC-10: 11-methacryloyloxy-1,1-undecanedicarboxylic acid
  4-META: 4-methacryloyloxyethyl trimellitate anhydride
Component (K)
  HEMA: 2-hydroxyethyl methacrylate
  GM: 2,3-dihydroxypropyl methacrylate
Other Optional Components
  HOMS: 2-methacryloyloxyethyl hydrogen succinate
  MMA: methyl methacrylate
(2) Adhesive Strength to Enamel and Dentin
Foreteeth of cattle were removed within 24 hours after slaughter, and the flat surface of enamel or dentin was prepared by shaving the foreteeth with #800 emery paper such that it was parallel to the surface of a lip under injection of water. Thereafter, compressed air was blown over the surface for about 10 seconds to dry it, an adhesive double coated tape having a 4 mm-diameter hole was adhered to the flat surface, and then paraffin wax having a hole of 1.5 mm in thickness and 6 mm in diameter was fixed on the above hole concentrically to prepare a mimic cavity. The dental composition of the present invention prepared immediately before its use was applied thinly to the inside of this mimic cavity and left for 20 seconds. Thereafter, compressed air was blown into the cavity for about 10 seconds to dry the dental composition. An adhesive was then applied to the dental composition and exposed to a visible light illuminator (Whitelight manufactured by Takara Bermont Co.) for 10 seconds to cure it. A dental composite resin (Palfeeklite Posteria (?)manufactured by Tokuyama Corporation) was further charged into the cavity and exposed to a visible light illuminator for 30 seconds to prepare an adhesion test sample.

The above adhesion test sample was immersed into water heated at 37° C. for 24 hours and then pulled at a cross-head speed of 10 mm/min using a tensile tester (Autograph manufactured by Shimadzu Corporation) to measure the tensile adhesive strengths of the tooth and the composite resin.

The tensile adhesive strengths of four test samples per test were measured by the above method and an average of the measurement values was taken as adhesive strength.

Enamel requires an adhesive strength of 17 MPa or more and dentin requires an adhesive strength of 15 MPa or more in order to inhibit formation of a gap between a filler material and the surface of a tooth and to prevent a filler material from falling off.
(3) Marginal Adaptability
Foreteeth of cattle were removed within 24 hours after slaughter, and the flat surface of enamel was prepared by shaving the foreteeth with #800 emery paper such that it was parallel to the surface of a lip under injection of water. Thereafter, a cavity having an inner diameter of 4.5 to 5 mm and a depth of 4 to 5 mm and reaching as far as dentin was formed using a carborundum point (HP35 manufactured by Shofu Inc.) under injection of water. The primer composition of the present invention was applied thinly to the inside of this cavity and left for 20 seconds. Thereafter, compressed air was blown into the cavity for about 5 seconds to dry it. An adhesive was then applied to the primer composition and exposed to a visible light illuminator (Witelight manufactured by Takara Bermont Co.) for 10 seconds to cure it. A dental composite resin (Palfique Estelite manufactured by Tokuyama Corporation) was further charged into the cavity and exposed to a visible light illuminator for 30 seconds to prepare a marginal adaptability test sample.

The above test sample was immersed into water heated at 37° C. for 24 hours and polished with #800 emery paper to remove excess composite resin under injection of water. Then a root portion of the tooth was covered with a polymerizable resin (Tokuso Cure Fast manufactured by Tokuyama Corporation) immediately. This sample was immersed into aqueous coloring matter solutions (0.1% basic fuchsine manufactured by Tokyo Kasei Co.) heated at 4° C. and 60° C. alternately 60 times each for 1 minute. After immersion, the test sample was ground with #120 emery paper so that its section in a crown direction could be seen from a cervical direction and how a coloring matter penetrated into the interface between the tooth and the composite resin was observed and evaluated. Evaluation was carried out by observing 12 sections of 6 test samples which consist of 6 sections on the side of cervix and 6 sections on the side of crown and counting the number of sections into which the coloring matter had penetrated. That is, the larger the number of sections the better marginal adaptability becomes.
(4) Preservation Stability
Components (A), (B) and (G) were dissolved into component (D). Immediately after this mixture solution was prepared, it was kept under airtight condition at 37° C. for two weeks and mixed with a predetermined amount of component (C) to prepare a primer. The adhesive strength of the primer was measured.

(5) Preparation of an Adhesive

Adhesives A to V having compositions shown in Table 1 were obtained as viscous liquids by stirring and mixing components under shielded light. Adhesive W is a bonding agent available as an accessory for Clearfil Liner Bond 2, a commercial adhesive.

g of distilled water. The resulting primer was used to treat the surface of a tooth, and adhesion was performed using adhesive A. Adhesion to enamel and dentin was measured. Results are shown in Table 2.

EXAMPLES 2 to 14

Primers were prepared in the same manner as in Example 1 and evaluated using adhesive A. The compositions of the primers and the results of evaluation are shown in Table 2.

TABLE 1

| | Adhesive composition (parts by weight) | | | | | | | | | | | | | | |
|---|---|---|---|---|---|---|---|---|---|---|---|---|---|---|---|
| | Component H | | Component J | | Component G | | | | Component K | | Optional component | | Polymerization initiator (I) | | |
| | MTS | 4-TAPT | MAC-10 | 4-META | 3G | BisGMA | NPG | D-2.6E | HEMA | GM | HOMS | MMA | CQ | DMBE | DAAP |
| A | — | — | — | — | 32 | 48 | — | — | 20 | — | — | — | 0.5 | 0.5 | — |
| B | — | — | — | — | 34 | 21 | — | — | 15 | — | 30 | — | 0.5 | 0.6 | — |
| C | 30 | — | — | — | 46 | 24 | — | — | — | — | — | — | 0.5 | 0.5 | — |
| D | 30 | — | — | — | 24 | 36 | — | — | — | — | — | 10 | 0.5 | 0.5 | — |
| E | 30 | — | — | — | 46 | 24 | — | — | — | — | — | — | 0.5 | 0.5 | — |
| F | 30 | — | — | — | — | 40 | 30 | — | — | — | — | — | 0.5 | 0.5 | — |
| G | 60 | — | — | — | 20 | — | — | — | 20 | — | — | — | 0.5 | 0.5 | — |
| H | 60 | — | — | — | 20 | — | — | — | 20 | — | — | — | 0.5 | — | 0.6 |
| I | 60 | — | — | — | 40 | — | — | — | — | — | — | — | 0.5 | 0.5 | — |
| J | 80 | — | — | — | — | — | — | — | 20 | — | — | — | 0.4 | 0.6 | — |
| K | — | 70 | — | — | 30 | — | — | — | — | — | — | — | 0.5 | 0.5 | — |
| L | 30 | — | 10 | — | 24 | 36 | — | — | — | — | — | — | 0.5 | 0.5 | — |
| M | — | — | 10 | — | 36 | 54 | — | — | — | — | — | — | 0.5 | 0.5 | — |
| N | — | — | 10 | — | 35 | 35 | — | — | 20 | — | — | — | 0.5 | 0.5 | — |
| O | — | — | 10 | — | 25 | 35 | — | — | 20 | — | 10 | — | 0.5 | 0.5 | — |
| P | — | — | 15 | — | — | — | 30 | 30 | — | 25 | — | — | 0.5 | 0.5 | — |
| Q | — | — | 20 | — | 36 | 24 | — | — | 20 | — | — | — | 0.5 | 0.5 | — |
| R | — | — | 30 | — | 34 | 21 | — | — | 15 | — | — | — | 0.5 | 0.6 | — |
| S | — | — | 30 | — | 25 | — | — | 25 | 20 | — | — | — | 0.5 | 0.6 | — |
| T | — | — | 30 | — | — | 18 | 32 | — | 20 | — | — | — | 0.5 | 0.6 | — |
| U | — | — | 30 | — | 30 | 20 | — | — | — | 20 | — | — | 0.5 | 0.6 | — |
| V | — | — | — | 10 | 41 | 29 | — | — | 20 | — | — | — | 0.5 | 0.6 | — |

Adhesives A and B contain none of components (H) and (J). Adhesives C to K contain component (H), adhesive L contains components (H) and (J), adhesives M to V contains all components (J), (K) and (G), and adhesive M contains components (J) and (G), but not component (K).

EXAMPLE 1

3.5 g of PM and 1.5 g of MAC-10 were dissolved in 5.0

COMPARATIVE EXAMPLES 1 to 7

Primers were prepared in the same manner as in Example 1 and evaluated using adhesive A. The compositions of the primers and the results of evaluation are shown in Table 2.

TABLE 2

| | Primer composition (% by weight) | | | | | | | | | | | Adhesive Strength/ MPa(SD) | |
|---|---|---|---|---|---|---|---|---|---|---|---|---|---|
| | Component A | | | Component B | | | | Phosphoric acid | Component D | | Component C | | |
| | PM | Phenyl-P | PM2 | MAC-10 | 4-META | MTS | HOMS | | EtOH | DME | H$_2$O | Dentin | Enamel |
| Ex. 1 | 35 | — | — | 15 | — | — | — | — | — | — | 50 | 15.8(2.8) | 18.6(2.2) |
| Ex. 2 | — | 10 | — | 10 | — | — | — | — | 25 | — | 55 | 19.1(3.5) | 23.1(4.3) |
| Ex. 3 | — | 10 | — | 10 | — | — | — | — | 36 | — | 44 | 20.3(2.8) | 20.1(3.4) |
| Ex. 4 | — | 20 | — | 8 | — | — | — | — | 50 | — | 22 | 20.7(3.9) | 18.8(2.1) |
| Ex. 5 | — | 7 | — | 11 | — | — | — | — | 12 | — | 70 | 17.9(1.4) | 20.4(2.8) |
| Ex. 6 | — | 15 | — | 5 | — | — | — | — | 24 | — | 56 | 17.1(1.8) | 24.7(4.5) |
| Ex. 7 | — | 10 | — | 25 | — | — | — | — | 20 | — | 45 | 20.0(2.7) | 20.8(2.0) |
| Ex. 8 | 10 | — | — | 10 | — | — | — | — | 25 | — | 55 | 16.8(2.4) | 20.1(3.4) |
| Ex. 9 | — | — | 10 | 10 | — | — | — | — | 25 | — | 55 | 17.1(3.1) | 22.5(4.0) |
| Ex. 10 | — | 10 | — | — | 10 | — | — | — | 27 | — | 55 | 18.4(1.4) | 19.8(2.6) |
| Ex. 11 | — | 10 | — | — | — | 8 | — | — | 27 | — | 55 | 18.2(3.2) | 21.1(3.3) |
| Ex. 12 | — | 15 | — | 8 | — | 2 | — | — | 25 | — | 50 | 18.7(2.9) | 25.8(4.1) |
| Ex. 13 | — | 10 | — | 10 | — | — | — | — | — | 24 | 53 | 18.6(1.5) | 21.3(0.9) |

TABLE 2-continued

| | Primer composition (% by weight) | | | | | | | | | | | | Adhesive Strength/ MPa(SD) | |
|---|---|---|---|---|---|---|---|---|---|---|---|---|---|---|
| | Component A | | | Component B | | | Optional component | | Component D | | Compo-nent C | | | |
| | PM | Phenyl-P | PM2 | MAC-10 | 4-META | MTS | HOMS | Phosphoric acid | EtOH | DME | H$_2$O | | Dentin | Enamel |
| Ex. 14 | — | 10 | — | 8 | — | — | — | — | 10 | 20 | 52 | | 19.6(2.4) | 23.0(2.7) |
| Comp. Ex. 1 | — | — | — | 20 | — | — | — | — | 25 | — | 55 | | 11.2(2.3) | 6.1(1.4) |
| Comp. Ex. 2 | — | — | — | 10 | — | — | — | 8 | 27 | — | 55 | | 7.8(1.1) | 20.9(3.0) |
| Comp. Ex. 3 | — | 62 | — | 8 | — | — | — | — | 15 | — | 15 | | 4.8(0.7) | 8.4(1.1) |
| Comp. Ex. 4 | — | 10 | — | — | — | — | — | — | 30 | — | 60 | | 13.7(4.1) | 21.6(3.3) |
| Comp. Ex. 5 | — | 10 | — | 60 | — | — | — | — | 15 | — | 15 | | 7.4(1.7) | 5.6(2.0) |
| Comp. Ex. 6 | — | 10 | — | — | — | — | 8 | — | 27 | — | 55 | | 12.0(2.6) | 21.1(2.6) |
| Comp. Ex. 7 | — | 10 | — | 8 | — | — | — | — | 80 | — | 2 | | 12.5(3.7) | 8.8(2.3) |

It is obvious from Example 1 that sufficient adhesive strengths to both enamel and dentin can be obtained and the object of the present invention can be attained when components (A), (B) and (C) are contained. Examples 2 to 7 show results obtained by using Phenyl-P as component (A), MAC-10 as component (B), and EtOH as component (D) and by changing their amounts. Examples 8 and 9 show results obtained by using different components as component (A), Examples 10 and 11 results obtained by using different components as component (B), Example 12 a result obtained by using a plurality of components as component (B), Example 13 a result obtained by using a different component as component (D), and Example 14 a result obtained by using a plurality of components as component (D). All the above Examples exhibited excellent adhesive strength to both enamel and dentin.

In contrast, Comparative Example 1 shows a result obtained without component (A) and exhibited low adhesive. strength to both enamel and dentin. Comparative Example 2 shows a result obtained by using phosphoric acid having no polymerizable unsaturated group in place of component (A) and exhibited low adhesive strength to dentin. Comparative Example 3 shows a result obtained by using component (A) in an amount beyond the specified range and exhibited low adhesive strength to both enamel and dentin. Comparative Example 4 shows a result obtained without component (B), and Comparative Example 6 a result obtained by using HOMS having only one carboxyl group in place of component (B). Both examples exhibited low adhesive strength to dentin. Comparative Example 5 shows a result obtained by using component (B) in an amount beyond the specified range and Comparative Example 7 a result obtained by using component (C) in an amount below the specified range. Both examples exhibited low adhesive strength to both enamel and dentin.

EXAMPLES 15 to 23

Primers were prepared in the same manner as in Example 1 and evaluated using adhesive M or N. The compositions of the primers and the results of evaluation. are shown in Table 3.

COMPARATIVE EXAMPLES 8 to 17

Primers were prepared in the same manner as in Example 1 and evaluated using adhesive M or N. The compositions of the primers and the results of evaluation are shown in Table 3.

TABLE 3

| | Primer composition (% by weight) | | | | | | | | | | | | Adhesive Strength/ MPa(SD) | |
|---|---|---|---|---|---|---|---|---|---|---|---|---|---|---|
| | Component A | | | Component B | | | Optional component | | Component D | | Compo-nent C | | | |
| | PM | Pheny 1-P | PM2 | MAC-10 | MTS | HOMS | Phosphoric acid | EtOH | IPA | H$_2$O | Adhesive | | Dentin | Enamel |
| Ex. 15 | — | 10 | — | 10 | — | — | — | 25 | — | 55 | M | | 19.7(2.1) | 23.1(3.9) |
| Ex. 16 | — | 12 | — | 8 | — | — | — | 10 | 15 | 55 | M | | 20.1(4.1) | 20.0(3.4) |
| Ex. 17 | — | 20 | — | 12 | — | — | — | 40 | — | 28 | M | | 18.1(1.8) | 19.3(3.2) |
| Ex. 18 | — | 10 | — | — | 8 | — | — | — | 27 | 55 | M | | 19.0(4.5) | 22.4(4.1) |
| Ex. 19 | — | 15 | — | — | 5 | — | — | 28 | — | 52 | M | | 18.3(2.8) | 24.5(2.6) |
| Ex. 20 | 10 | — | — | 8 | — | — | — | 27 | — | 55 | N | | 16.8(1.6) | 19.7(3.6) |
| Ex. 21 | — | 10 | — | 8 | — | — | — | 27 | — | 55 | N | | 24.3(2.8) | 22.6(2.2) |
| Ex. 22 | 12 | — | 12 | 8 | — | — | — | 26 | — | 54 | N | | 18.3(1.9) | 20.8(2.1) |
| Ex. 23 | — | 5 | 5 | 8 | — | — | — | 27 | — | 55 | N | | 20.2(2.4) | 21.7(3.0) |
| Comp. | — | — | — | 15 | — | — | — | 27 | — | 58 | M | | 10.7(1.8) | 7.0(0.5) |

TABLE 3-continued

| | Primer composition (% by weight) | | | | | | | | | | Adhesive Strength/ MPa(SD) | |
|---|---|---|---|---|---|---|---|---|---|---|---|---|
| | Component A | | | Component B | | Optional component | | Component D | | Compo-nent C | | |
| | PM | Pheny 1-P | PM2 | MAC-10 | MTS | HOMS | Phosphoric acid | EtOH | IPA | H$_2$O | Adhesive | Dentin | Enamel |
| Ex. 8 Comp. Ex. 9 | — | — | — | 10 | — | — | 8 | 27 | — | 55 | M | 8.5(2.4) | 20.1(3.8) |
| Comp. Ex. 10 | — | 62 | — | 8 | — | — | — | 15 | — | 15 | M | 5.1(0.8) | 7.4(1.2) |
| Comp. Ex. 11 | — | 10 | — | — | — | — | — | 30 | — | 60 | M | 13.6(1.4) | 21.5(3.2) |
| Comp. Ex. 12 | — | 10 | — | — | — | 10 | — | 25 | — | 55 | M | 12.7(2.5) | 21.6(4.7) |
| Comp. Ex. 13 | — | 10 | — | 8 | — | — | — | 80 | — | 2 | M | 10.1(4.7) | 7.6(1.0) |
| Comp. Ex. 14 | — | — | — | 15 | — | — | — | 27 | — | 58 | N | 12.0(3.7) | 5.8(0.9) |
| Comp. Ex. 15 | — | — | — | 10 | — | — | 8 | 27 | — | 55 | N | 8.4(2.0) | 18.9(3.4) |
| Comp. Ex. 16 | — | 62 | — | 8 | — | — | — | 15 | — | 15 | N | 5.5(1.4) | 7.3(2.2) |
| Comp. Ex. 17 | — | 10 | — | 8 | — | — | — | 80 | — | 2 | N | 9.8(3.9) | 5.7(0.7) |

Examples 15 to 19 show results obtained by using adhesive M and changing kinds and amounts of components (A), (B) and (D) and Examples 20 to 23 results obtained by using adhesive N and changing kinds and amounts of components (A), (B) and (D). Examples 15, 20 and 21 show results obtained by using different components as component (A), Example 16 a result obtained by using a plurality of components as component (D), Example 17 a result obtained by reducing the amount of component (C), Examples 15, 18 and 19 results obtained by changing components (B) and (D), and Examples 22 and 23 results obtained by using a plurality of components as component (A). All the above examples obtained sufficient adhesive strength to both enamel and dentin.

Comparative Examples 8 and 14 show results obtained without component (A) and exhibited low adhesive strength to both enamel and dentin. Comparative Examples 9 and 15 show results obtained by using phosphoric acid having no polymerizable unsaturated group in place of component (A) and exhibited low adhesive strength to dentin. Comparative Examples 10 and 16 show results obtained by using component (A) in an amount above the specified range and exhibited low adhesive strength to both enamel and dentin. Comparative Examples 11 and 17 show results obtained without component (B) and Comparative Example 12 a result obtained by using HOMS having only one carboxyl group in place of component (B). Both comparative examples exhibited low adhesive strength to dentin.

EXAMPLES 24 to 36

Primers were prepared in the same manner as in Example 1 and evaluated using different adhesives. The compositions of the primers, used adhesives and results are shown in Table 4.

TABLE 4

| | Primer composition (% by weight) | | | | | Adhesive strength/ MPa(SD) | |
|---|---|---|---|---|---|---|---|
| | Component A | Component B | Component D | Component C | | | |
| | Phenyl-P | MTS | IPA | H$_2$O | Adhesive | Dentin | Enamel |
| Ex. 24 | 10 | 8 | 27 | 55 | B | 21.4(2.2) | 21.5(4.0) |
| Ex. 25 | 10 | 8 | 27 | 55 | D | 20.5(2.4) | 23.6(2.4) |
| Ex. 26 | 10 | 8 | 27 | 55 | G | 22.2(2.9) | 21.1(4.9) |
| Ex. 27 | 10 | 8 | 27 | 55 | H | 21.8(2.4) | 22.3(3.0) |
| Ex. 28 | 10 | 8 | 27 | 55 | I | 22.9(4.9) | 25.8(3.6) |
| Ex. 29 | 10 | 8 | 27 | 55 | J | 24.0(2.5) | 21.3(2.2) |
| Ex. 30 | 10 | 8 | 27 | 55 | K | 20.7(2.8) | 20.7(3.7) |
| Ex. 31 | 10 | 8 | 27 | 55 | L | 21.5(2.6) | 19.9(2.0) |
| Ex. 32 | 10 | 8 | 27 | 55 | O | 18.8(2.4) | 22.6(3.7) |
| Ex. 33 | 10 | 8 | 27 | 55 | P | 18.4(4.0) | 21.5(3.5) |
| Ex. 34 | 10 | 8 | 27 | 55 | S | 17.9(2.3) | 23.3(1.1) |
| Ex. 35 | 10 | 8 | 27 | 55 | V | 17.2(2.2) | 21.3(2.5) |
| Ex. 36 | 10 | 8 | 27 | 55 | W | 17.0(2.4) | 21.3(3.3) |

In Examples 24 to 36, test samples were treated with primers which contained phenyl-P as component (A), MTS as component (B) and IPA as component (D), and measured for their adhesive strengths using adhesives having various compositions. All the examples exhibited good adhesive strength to both enamel and dentin. It is obvious from this fact that adhesive strength is not restricted by the composition of an adhesive.

EXAMPLES 37 to 53

Primers were prepared in the same manner as in Example 1 and evaluated using adhesive G. The compositions of the primers and results are shown in Table 5.

COMPARATIVE EXAMPLES 18 to 20

Primers were prepared in the same manner as in Example 1 and evaluated using adhesive G. The compositions of the primers and results are shown in Table 5.

examples exhibited good adhesive strength to both enamel and dentin. Examples 45 and 46 show results obtained by including component (F) and exhibited good adhesive strength. Examples 47 to 49 show results obtained by blending component (G). Examples 47 and 48 show results obtained by using different components as component (G), and Examples 48 and 49 results obtained by using different components as component (D). Examples 50 and 51 show results obtained by blending both components (E) and (G), and Examples 52 and 53 results obtained by blending both components (F) and (G). All the examples exhibited good adhesive strength.

Comparative Example 18 shows a result obtained without component (A) and exhibited low adhesive strength to dentin. Comparative Example 19 shows a result obtained by using component (B) in an amount above the specified range and exhibited low adhesive strength to both enamel and

TABLE 5

| | Primer composition (% by weight) | | | | | | | | | | | | | | Adhesive strength/ MPa(SD) | |
|---|---|---|---|---|---|---|---|---|---|---|---|---|---|---|---|---|
| | Component A | | Component B | | Component E | | | Component F | Component G | | Component D | | Component C | | | |
| | Phenyl-P | PM | MTS | MAC-10 | HNO$_3$ | HCl | DBS | AMPS | 3G | NPG | EtOH | DME | H$_2$O | | Dentin | Enamel |
| Ex. 37 | 3 | — | 8 | — | 1.2 | — | — | — | — | — | 29 | — | 58.8 | | 22.0(2.9) | 20.2(2.4) |
| Ex. 38 | 3 | — | 8 | — | 0.6 | — | — | — | — | — | 29 | — | 59.4 | | 20.7(3.6) | 19.3(2.9) |
| Ex. 39 | 3 | — | 8 | — | 1.2 | — | — | — | — | — | 14 | — | 73.8 | | 18.2(3.2) | 22.8(3.7) |
| Ex. 40 | — | 3 | 8 | — | 1.2 | — | — | — | — | — | 29 | — | 58.8 | | 15.2(3.4) | 22.4(3.2) |
| Ex. 41 | 3 | — | — | 8 | 1.2 | — | — | — | — | — | 29 | — | 58.8 | | 16.5(2.6) | 20.2(2.9) |
| Ex. 42 | 3 | — | — | 16 | 1.2 | — | — | — | — | — | 31 | — | 48.8 | | 19.5(1.9) | 21.3(2.8) |
| Ex. 43 | 3 | — | 8 | — | — | 1.0 | — | — | — | — | 29 | — | 59.0 | | 19.2(2.7) | 20.8(3.3) |
| Ex. 44 | 3 | — | 8 | — | — | — | 2.0 | — | — | — | 29 | — | 58.0 | | 15.5(2.5) | 18.5(3.1) |
| Ex. 45 | 3 | — | 8 | — | — | — | — | 2 | — | — | 29 | — | 58.8 | | 15.7(1.9) | 17.4(1.8) |
| Ex. 46 | 6 | — | 8 | — | — | — | — | 2 | — | — | 25 | — | 59.0 | | 17.7(2.1) | 19.6(2.5) |
| Ex. 47 | 12 | — | 8 | — | — | — | — | — | 4 | — | 23 | — | 53.0 | | 20.8(2.4) | 22.4(2.2) |
| Ex. 48 | 12 | — | 8 | — | — | — | — | — | — | 2 | 25 | — | 53.0 | | 18.6(2.7) | 21.0(1.9) |
| Ex. 49 | 13 | — | 8 | — | — | — | — | — | — | 2 | — | 25 | 52.0 | | 19.1(2.3) | 20.8(2.5) |
| Ex. 50 | 3 | — | 8 | — | 1.2 | — | — | — | 5 | — | 24 | — | 58.8 | | 18.8(1.9) | 23.3(3.0) |
| Ex. 51 | 3 | — | — | 8 | 1.2 | — | — | — | 5 | — | 24 | — | 58.8 | | 17.8(2.1) | 19.8(2.6) |
| Ex. 52 | 3 | — | 8 | — | — | — | — | 2 | — | 2 | 30 | — | 55.0 | | 16.4(2.4) | 19.0(3.2) |
| Ex. 53 | 5 | — | 8 | — | — | — | — | 2 | — | 2 | — | 28 | 55.0 | | 16.4(2.4) | 19.0(3.2) |
| Comp. Ex. 18 | — | — | 15 | — | 1.2 | — | — | — | — | — | 35 | — | 58.8 | | 10.1(2.0) | 18.6(4.7) |
| Comp. Ex. 19 | 3 | — | 57 | — | 2.0 | — | — | — | — | — | 15 | — | 23.0 | | 8.8(1.3) | 9.7(2.7) |
| Comp. Ex. 20 | 3 | — | 8 | — | 1.2 | — | — | — | — | — | 87.8 | — | — | | 8.5(1.7) | 5.4(1.4) |

Examples 37 to 53 show results obtained by blending components (E), (F) and (G) in addition to components (A), (B), (C) and (D). Examples 37 to 44 contain component (E). Examples 37 to 39 show results obtained by changing the amounts of components (E) and (C), Example 40 a result obtained by using a different component as component (A), Examples 41 and 42 results obtained by using different components as component (B) and changing the amount of component (B), and Examples 43 and 44 results obtained by using different components as component (E). All the dentin. Comparative Example 20 shows a result obtained without component (C) and exhibited low adhesive strength to both enamel and dentin.

EXAMPLES 54 to 63

Primers were prepared in the same manner as in Example 1 and evaluated using different adhesives. The compositions of the primers, used adhesives and results are shown in Table 6.

TABLE 6

| | Primer composition (% by weight) | | | | | | | | | Adhesive strength/ MPa(SD) | |
|---|---|---|---|---|---|---|---|---|---|---|---|
| | Component A | Component B | Component E | Component F | Component G | | Component D | Component C | | | |
| | Phenyl-P | MTS | HNO$_3$ | AMPS | 3G | NPG | EtOH | H$_2$O | Adhesive | Dentin | Enamel |
| Ex. 54 | 3 | 8 | 1.2 | — | — | — | 29 | 58.8 | A | 16.1(3.2) | 22.3(1.9) |
| Ex. 55 | 3 | 8 | 1.2 | — | — | — | 29 | 58.8 | M | 16.9(1.7) | 23.1(3.5) |
| Ex. 56 | 3 | 8 | 1.2 | — | — | — | 29 | 58.8 | N | 17.1(1.3) | 22.5(1.8) |
| Ex. 57 | 3 | — | 1.2 | — | — | — | 29 | 58.8 | M | 16.2(2.6) | 19.8(2.6) |
| Ex. 58 | 3 | 8 | 0.6 | — | — | — | 29 | 59.4 | N | 21.2(1.7) | 19.3(2.5) |
| Ex. 59 | 3 | — | — | 2 | — | — | 29 | 58.0 | N | 16.3(2.0) | 18.9(2.3) |
| Ex. 60 | 12 | 8 | — | — | — | 2 | 25 | 53.0 | N | 20.7(2.4) | 21.8(2.6) |
| Ex. 61 | 3 | 8 | 1.2 | — | 5 | — | 24 | 58.8 | A | 16.8(1.8) | 21.1(2.5) |
| Ex. 62 | 3 | 8 | 1.2 | — | 5 | — | 24 | 58.8 | M | 17.0(2.5) | 20.8(3.2) |
| Ex. 63 | 3 | 8 | 1.2 | — | 5 | — | 24 | 58.8 | N | 18.4(2.4) | 19.8(2.9) |

In Examples 54 to 63, test samples were treated with primers which contained components (E), (F) and (G) in addition to components (A), (B), (C) and (D) and measured for their adhesive strength using adhesive having different compositions. All the examples exhibited good adhesive strength to both enamel and dentin. Therefore, it is obvious that adhesive strength is not restricted by the composition of an adhesive.

EXAMPLES 64 to 71

Primers were prepared in the same manner as in Example 1 and evaluated for their marginal adaptability using different adhesives. The compositions of the primers, used adhesives and results are shown in Table 7.

COMPARATIVE EXAMPLES 21 and 22

Primers were prepared in the same manner as in Example 1 and evaluated for their marginal adaptability using adhesive N. The compositions of the primers and the results of the evaluation are shown in Table 7.

All Examples 64 to 71 exhibited good marginal adaptability compared with Comparative Example 21 which did not contain component (A) and Comparative Example 22 which did not contain component (C). Moreover, Examples 67 to 71 containing component (G) exhibited higher marginal adaptability than Examples 64 to 66 which did not contain component (G).

EXAMPLES 72 to 74

1.0 g of phenyl-P and 0.8 g of MAC-10 were dissolved in 2.7 g of DME (Example 72), 2.7 g of DME with 0.2 g of NPG (Example 74) or 2.7 g of BMEE (Example 73) as a water-soluble ether having no hydroxyl group and the preservation stability test carried out on these combinations. Adhesive G was used in the test. The compositions of the primers and results are shown in Table 8.

TABLE 7

| | Primer composition (% by weight) | | | | | | | | Marginal adaptability |
|---|---|---|---|---|---|---|---|---|---|
| | Component A | Component B | Component E | Component G | | Component D | Component C | | |
| | Phenyl-P | MAC-10 | HNO$_3$ | 3G | NPG | EtOH | H$_2$O | Adhesive | n/12 |
| Ex. 64 | 12 | 8 | — | — | — | 27 | 53 | G | 5 |
| Ex. 65 | 12 | 8 | — | — | — | 27 | 53 | N | 4 |
| Ex. 66 | 3 | 8 | 1.2 | — | — | 29 | 58.8 | N | 6 |
| Ex. 67 | 12 | 8 | — | — | 2 | 27 | 51 | G | 10 |
| Ex. 68 | 12 | 8 | — | — | 2 | 27 | 51 | N | 9 |
| Ex. 69 | 15 | 5 | — | 4 | — | 26 | 50 | N | 10 |
| Ex. 70 | 16 | 8 | — | — | 2 | 23 | 51 | Q | 11 |
| Ex. 71 | 3 | 8 | 1.2 | — | 4 | 27 | 56.8 | N | 9 |
| Comp. Ex. 21 | — | 15 | — | — | — | 27 | 58 | N | 0 |
| Comp. Ex. 22 | 12 | 8 | — | — | — | 80 | — | N | 0 |

TABLE 8

| | Primer composition (% by weight) | | | | | Adhesive strength/ MPa(SD) | | Adhesive strength after storage/MPa(SD) | |
|---|---|---|---|---|---|---|---|---|---|
| | Component A | Component B | Component G | Component D | | Component C | | | |
| | Phenyl-P | MAC-10 | NPG | DME | BMEE | H$_2$O | Dentin | Enamel | Dentin | Enamel |
| Ex. 72 | 10 | 8 | — | 27 | — | 55 | 20.5(2.2) | 22.4(3.1) | 19.7(2.0) | 21.4(4.0) |
| Ex. 73 | 10 | 8 | — | — | 27 | 55 | 19.4(2.7) | 23.6(2.7) | 21.0(2.1) | 22.9(3.4) |
| Ex. 74 | 10 | 8 | 2 | 27 | — | 53 | 21.6(2.0) | 24.9(3.3) | 20.7(2.7) | 25.6(4.2) |

The primers of Examples 72 to 74 exhibited the same adhesive strength before and after preservation. Their preservation stabilities were good.

EXAMPLES 75 to 90

Primers were prepared in the same manner as in Example 1 and evaluated for their adhesive strength using adhesive C or R. The compositions of the primers, used adhesives and results are shown in Table 9.

COMPARATIVE EXAMPLES 23 to 28

Primers were prepared in the same manner as in Example 1 and evaluated for their adhesive strength using adhesive C or R. The compositions of the primers, used adhesives and results are shown in Table 9.

EXAMPLES 91 to 113

Primers were prepared in the same manner as in Example 1 and evaluated for their adhesive strength using different adhesives. The compositions of the primers, used adhesives and results are shown in Table 10.

COMPARATIVE EXAMPLES 29 to 31

Primers were prepared in the same manner as in Example 1 and evaluated for their adhesive strength using different adhesives. The compositions of the primers, used adhesives and results are shown in Table 10.

TABLE 9

| | Primer composition (% by weight) | | | | | | | | | Adhesive Strength/ MPa(SD) | |
|---|---|---|---|---|---|---|---|---|---|---|---|
| | Component A | | | Optional component Phosphoric | Component D | | | Component C | | | |
| | PM | Phenyl-P | PM2 | acid | HEMA | EtOH | DME | H$_2$O | Adhesive | Dentin | Enamel |
| Ex. 75 | 10 | — | — | — | — | 30 | — | 60 | C | 16.4(2.4) | 21.4(2.1) |
| Ex. 76 | — | 10 | — | — | — | 30 | — | 60 | C | 18.8(2.1) | 20.1(2.4) |
| Ex. 77 | — | — | 12 | — | — | 28 | — | 60 | C | 18.0(2.1) | 21.3(2.5) |
| Ex. 78 | — | 10 | — | — | — | — | 30 | 60 | C | 18.4(2.6) | 22.5(2.7) |
| Ex. 79 | — | 10 | — | — | 8 | 22 | — | 60 | C | 18.8(1.6) | 18.9(1.0) |
| Ex. 80 | — | 18 | — | — | — | 22 | — | 60 | C | 18.1(1.8) | 19.7(3.2) |
| Ex. 81 | — | 35 | — | — | — | 15 | — | 50 | C | 17.0(2.4) | 21.4(3.8) |
| Ex. 82 | — | 18 | — | — | — | 57 | — | 25 | C | 16.3(1.9) | 20.5(1.6) |
| Ex. 83 | 10 | — | — | — | — | 30 | — | 60 | R | 16.0(1.8) | 22.4(3.1) |
| Ex. 84 | — | 10 | — | — | — | 30 | — | 60 | R | 17.3(2.0) | 21.2(2.1) |
| Ex. 85 | — | — | 10 | — | — | 30 | — | 60 | R | 17.0(3.0) | 20.7(1.9) |
| Ex. 86 | — | 10 | — | — | — | — | 30 | 60 | R | 18.1(2.2) | 18.9(2.6) |
| Ex. 87 | — | 10 | — | — | 8 | 22 | — | 60 | R | 19.4(2.4) | 19.9(0.7) |
| Ex. 88 | — | 18 | — | — | — | 22 | — | 60 | R | 16.1(1.5) | 22.6(3.5) |
| Ex. 89 | — | 35 | — | — | — | 15 | — | 50 | R | 17.2(0.8) | 20.2(2.6) |
| Ex. 90 | — | 18 | — | — | — | 57 | — | 25 | R | 16.1(1.4) | 18.5(2.5) |
| Comp. Ex. 23 | — | — | — | 10 | — | 30 | — | 60 | C | 9.7(2.1) | 20.6(4.7) |
| Comp. Ex. 24 | — | — | — | 10 | — | 30 | — | 60 | R | 9.5(2.4) | 18.9(3.1) |
| Comp. Ex. 25 | — | 60 | — | — | — | 10 | — | 30 | C | 9.1(2.3) | 18.0(2.9) |
| Comp. Ex. 26 | — | 60 | — | — | — | 10 | — | 30 | R | 7.8(2.2) | 18.8(2.9) |
| Comp. Ex. 27 | — | 15 | — | — | — | 85 | — | — | C | 10.6(1.7) | 7.3(2.9) |
| Comp. Ex. 28 | — | 15 | — | — | — | 85 | — | — | R | 11.0(1.5) | 6.8(2.0) |

TABLE 10

| | Primer composition (% by weight) | | | | | Adhesive Strength/ MPa(SD) | |
|---|---|---|---|---|---|---|---|
| | Component A | Component D | | | Component C | | |
| | Phenyl-P | HEMA | EtOH | DME | H₂O | Adhesive | Dentin | Enamel |
| Ex. 91 | 10 | — | 30 | — | 60 | D | 16.8(1.3) | 24.1(1.8) |
| Ex. 92 | 10 | — | — | 30 | 60 | E | 17.5(2.1) | 22.1(2.7) |
| Ex. 93 | 10 | — | 30 | — | 60 | F | 17.1(2.4) | 22.7(3.3) |
| Ex. 94 | 10 | 8 | 27 | — | 55 | F | 17.1(2.7) | 22.5(2.5) |
| Ex. 95 | 10 | — | 30 | — | 60 | G | 19.8(3.6) | 23.6(2.9) |
| Ex. 96 | 10 | 8 | 30 | — | 55 | G | 20.9(0.5) | 22.5(2.0) |
| Ex. 97 | 10 | — | 30 | — | 60 | H | 18.6(2.7) | 22.5(2.8) |
| Ex. 98 | 10 | — | 30 | — | 60 | I | 16.7(2.7) | 23.3(2.2) |
| Ex. 99 | 10 | 8 | 27 | — | 55 | I | 17.8(1.8) | 20.1(1.9) |
| Ex. 100 | 10 | — | 30 | — | 60 | J | 18.8(2.5) | 23.1(2.3) |
| Ex. 101 | 10 | — | 30 | — | 60 | K | 17.1(2.4) | 20.1(2.0) |
| Ex. 102 | 10 | — | 30 | — | 60 | L | 18.4(2.3) | 23.7(3.4) |
| Ex. 103 | 10 | — | 30 | — | 60 | N | 21.6(3.8) | 23.7(2.4) |
| Ex. 104 | 10 | 8 | 27 | — | 55 | N | 20.3(4.4) | 21.9(3.2) |
| Ex. 105 | 10 | — | 30 | — | 60 | O | 18.9(3.5) | 22.9(2.7) |
| Ex. 106 | 10 | — | — | 30 | 60 | P | 16.7(1.8) | 22.4(3.0) |
| Ex. 107 | 10 | — | 30 | — | 60 | Q | 17.3(2.0) | 23.2(3.4) |
| Ex. 108 | 10 | — | 30 | — | 60 | S | 17.6(2.3) | 22.5(1.6) |
| Ex. 109 | 10 | — | 30 | — | 60 | T | 19.8(2.3) | 23.7(2.3) |
| Ex. 110 | 10 | 8 | 27 | — | 55 | T | 18.1(2.6) | 24.1(3.0) |
| Ex. 111 | 10 | — | 30 | — | 60 | U | 18.7(3.1) | 22.2(3.0) |
| Ex. 112 | 10 | 8 | 27 | — | 55 | U | 18.0(1.5) | 23.0(2.6) |
| Ex. 113 | 10 | — | 30 | — | 60 | V | 15.5(2.5) | 18.7(2.7) |
| Comp. Ex. 29 | 10 | — | 30 | — | 60 | A | 13.7(4.1) | 20.7(2.6) |
| Comp. Ex. 30 | 10 | — | 30 | — | 60 | B | 12.0(2.1) | 22.7(3.3) |
| Comp. Ex. 31 | 10 | — | 30 | — | 60 | M | 11.4(2.4) | 21.4(3.0) |

EXAMPLES 114 to 124

Primers were prepared in the same manner as in Example 1 and evaluated for their adhesive strength using different adhesives. The compositions of the primers, used adhesives and results are shown in Table 10.

TABLE 11

| | Primer composition (% by weight) | | | | | | | Adhesive Strength/ MPa(SD) | |
|---|---|---|---|---|---|---|---|---|---|
| | Component A | Component G | | | Optional component | Component D | Component C | | |
| | Phenyl-P | 3G | NPG | BisGMA | HOMS | EtOH | H₂O | Adhesive | Dentin | Enamel |
| Ex. 114 | 10 | 8 | — | — | — | 27 | 55 | C | 16.6(2.0) | 22.0(3.1) |
| Ex. 115 | 10 | 8 | — | — | — | 27 | 55 | G | 18.9(1.6) | 23.2(3.6) |
| Ex. 116 | 10 | 8 | — | — | — | 27 | 55 | N | 16.8(3.2) | 21.6(3.0) |
| Ex. 117 | 10 | 8 | — | — | — | 27 | 55 | R | 18.1(3.0) | 21.4(3.3) |
| Ex. 118 | 10 | 8 | — | — | — | 27 | 55 | U | 17.3(2.1) | 22.5(3.2) |
| Ex. 119 | 10 | — | 5 | — | — | 30 | 55 | G | 18.3(2.3) | 22.4(2.8) |
| Ex. 120 | 10 | — | 5 | — | — | 30 | 55 | N | 17.4(2.1) | 20.8(2.6) |
| Ex. 121 | 10 | — | — | 8 | — | 27 | 55 | C | 16.3(2.8) | 19.0(2.3) |
| Ex. 122 | 10 | — | — | 8 | — | 27 | 55 | R | 16.0(2.5) | 20.0(1.5) |
| Ex. 123 | 10 | — | — | — | 10 | 25 | 55 | C | 17.8(2.3) | 22.2(2.0) |
| Ex. 124 | 10 | — | — | — | 10 | 25 | 55 | R | 17.4(4.1) | 21.8(2.3) |

Examples 75 to 124 and Comparative Examples 26 to 34 show results obtained by using a composition which does not contain component (B) as a primer.

Examples 75 to 82 show results obtained by using a composition containing component (H) as adhesive C, Examples 83 to 90 results obtained by using a composition containing components (J), (K) and (G) as adhesive R, and Examples 75 to 77 and 83 to 85 results obtained by using different components as component (A). All these examples exhibited good adhesive strength. Examples 76, 80 to 82, 84 and 88 to 90 show results obtained by changing the amounts of components (A), (D) and (C) contained in the primers. Examples 79 and 86 show results obtained by using different components as component (D), and Examples 79 and 87 results obtained by substituting part of component (D) with HEMA, a water-soluble alcohol having a polymerizable unsaturated group. All the above examples exhibited good adhesive strength to both enamel and dentin.

Comparative Examples 26 and 27 show results obtained by using phosphoric acid having no polymerizable unsaturated group in place of component (A) in the primers, and Comparative Examples 28 and 29 results obtained by using component (A) in an amount above the specified range. All the comparative examples exhibited low adhesive strength to dentin. Comparative Examples 30 and 31 show results obtained without component (C) and exhibited low adhesive strength to both enamel and dentin.

Examples 91 to 113 show results obtained by using adhesives D to L, compositions which contain component (H) or adhesives N to V (excluding R), compositions which contain components (J), (K) and (G).

All the examples exhibited good adhesive strength to both enamel and dentin. It is understood that there is no problem if an adhesive having a composition satisfying the above conditions is used.

Comparative Example 32 shows a result obtained by using an adhesive which contains components (K) and (G), but not components (H) and (J), Comparative Example 33 a result obtained by using HOMS, a monomer having only one carboxyl group, in place of component (J), and Comparative Example 34 a result obtained by using an adhesive which contains components (J) and (G) but not components (H) and (K). All the comparative examples exhibited low adhesive strength to dentin. Therefore, it is understood from comparison with Examples 2, 15 and 24 that a specific adhesive satisfying the above conditions is required when component (B) is not contained in a primer.

Examples 114 to 124 show results obtained by adding component (G) or HOMS as an optional component in addition to components (A), (C) and (D). All the examples exhibited good adhesive strength to both enamel and dentin. Therefore, it is understood that addition of these components has no problem at all.

What is claimed is:

1. A primer for teeth which comprises (A) an unsaturated monomer containing a phosphoric acid group, (B) an unsaturated monomer containing a plurality of carboxylic acid groups, and (C) water, as main components, in amounts of 5 to 50% by weight, 1 to 50% by weight and 5 to 90% by weight, respectively, based on the weight of the composition, providing that the sum of said monomers (A) and (B) is 10% or more by weight, said monomers (A) and (B) being separate monomers.

2. The primer composition of claim 1 which comprises component (A) in an amount of 5 to 50% by weight.

3. The primer composition of claim 1 which further comprises (D) a water-soluble organic solvent in an amount of 1 to 80% by weight.

4. The primer composition of claim 3, wherein the water-soluble organic solvent (D) is an alcohol compound or an ether compound.

5. The primer composition of claim 1, wherein the phosphoric acid group-containing unsaturated monomer (A) is a monomer represented by the following general formula:

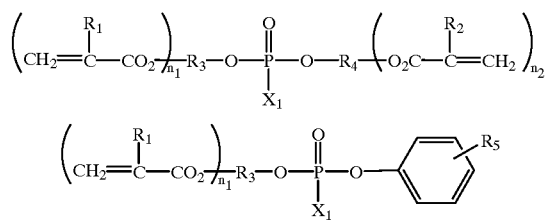

wherein each of $R_1$ and $R_2$ is independently hydrogen atom or a methyl group, each of $R_3$ and $R_4$ is independently an organic group having a valence of to 6 and 1 to 30 carbon atoms, which may have an ether linkage and/or an ester linkage, $R_5$ is hydrogen atom, an alkyl group having 1 to 5 carbon atoms or an alkoxyl group having 1 to 5 carbon atoms, $X_1$ is hydroxyl group, a mercapto group or a halogen atom, and $n_1$ and $n_2$ are each an integer of 1 to 5.

6. The primer composition of claim 1, wherein the carboxylic acid groups-containing unsaturated monomer is a monomer represented by the following general formula:

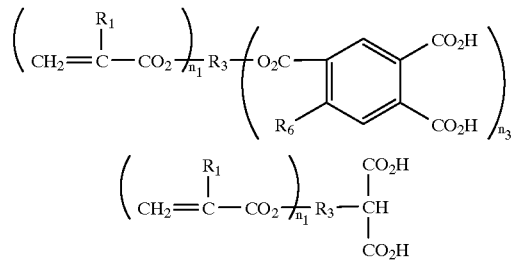

wherein $R_1$ is hydrogen atom or a methyl group, $R_3$ is an organic group having a valence of 2 to 6 and 1 to 30 carbon atoms, which may have an ether linkage and/or an ester linkage, $R_6$ is hydrogen atom or a carboxyl group, $n_1$ is an integer of 1 to 5, and $n_3$ is 1 or 2.

7. A primer composition for teeth which comprises (A) an unsaturated monomer containing a phosphoric acid group, (B) an unsaturated monomer containing a plurality of carboxylic acid groups, (C) water, (D) a water-soluble organic solvent, and (G) a polyfunctional monomer in amounts of 5 to 50% by weight, 1 to 50% by weight, 5 to 90% by weight, 1 to 80% by weight and 0.1 to 30% by weight, respectively, based on the weight of the composition, said monomers (A) and (B) being separate monomers.

8. A primer composition for teeth which comprises (A) an unsaturated monomer containing a phosphoric acid group, (B) an unsaturated monomer containing a plurality of carboxylic acid groups, (C) water, (D) a water-soluble organic solvent, and (F) a sulfonic acid group-containing monomer as main components in amounts of 0.5 to 7% by weight, 3 to 50% by weight, 5 to 90% by weight, 1 to 80% by weight, and 0.01 to 12% by weight, respectively, based on the composition, said monomers (A) and (B) being separate monomers.

9. The primer composition of claim 8, wherein the water-soluble organic solvent (D) is an alcohol compound or an ether compound.

10. The primer composition of claim 8 which further comprises (G) a polyfunctional unsaturated monomer in an amount of 0.1 to 30% by weight.

11. The primer composition of claim 8, wherein the phosphoric acid group-containing unsaturated monomer (A) is a monomer represented by the following general formula:

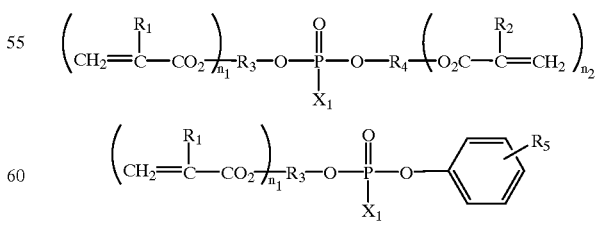

wherein each of $R_1$ and $R_2$ is independently hydrogen atom or a methyl group, each of $R_3$ and $R_4$ is independently an organic group having a valence of 2 to 6 and 1 to 30 carbon atoms, which may have an ether linkage and/or an ester linkage, $R_5$ is hydrogen atom, an alkyl group having 1 to 5 carbon atoms or an alkoxyl group having 1 to 5 carbon atoms, $X_1$ is a hydroxyl group, a mercapto group or a halogen atom, and $n_1$ and $n_2$ are independently an integer of 1 to 5.

12. The primer composition of claim 8, wherein the carboxylic acid groups-containing unsaturated monomer (B) is a monomer represented by the following general formula:

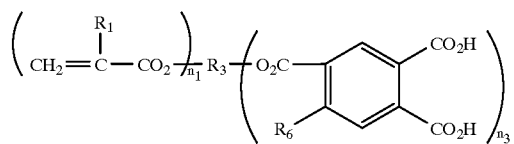

-continued

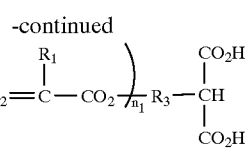

wherein $R_1$ is hydrogen atom or a methyl group, $R_3$ is an organic group having a valence of 2 to 6 and 1 to 30 carbon atoms, which may have an ether linkage and/or an ester linkage, $R_6$ is hydrogen atom or a carboxyl group, $n_1$ is an integer of 1 to 5, and $n_3$ is 1 or 2.

13. The primer composition of claim 1, which shows a tensile adhesive strength to enamel of at least 17 MPa and a tensile adhesive strength to dentin of at least 15 MPa.

* * * * *